(12) United States Patent
Nettekoven et al.

(10) Patent No.: US 7,745,479 B2
(45) Date of Patent: *Jun. 29, 2010

(54) 1,5-SUBSTITUTED INDOL-2-YL AMIDE DERIVATIVES

(75) Inventors: Matthias Nettekoven, Grenzach-Wyhlen (DE); Jean-Marc Plancher, Hagenthal-le-Bas (FR); Hans Richter, Grenzach-Wyhlen, DE (US); Olivier Roche, Folgensbourg (FR); Valerie Runtz-Schmitt, Rixheim (FR); Sven Taylor, Riedisheim (FR)

(73) Assignee: Hoffmann-La Roche Inc., Nutley, NJ (US)

( * ) Notice: Subject to any disclaimer, the term of this patent is extended or adjusted under 35 U.S.C. 154(b) by 578 days.

This patent is subject to a terminal disclaimer.

(21) Appl. No.: 11/604,412

(22) Filed: Nov. 27, 2006

(65) Prior Publication Data

US 2007/0123515 A1    May 31, 2007

(30) Foreign Application Priority Data

Nov. 30, 2005 (EP) .................................. 05111478

(51) Int. Cl.
*A61K 31/55* (2006.01)
*A61K 31/541* (2006.01)
*A61K 31/5377* (2006.01)
*A61K 31/454* (2006.01)
*A61K 31/4545* (2006.01)
*A61K 31/4045* (2006.01)
*C07D 209/42* (2006.01)
*C07D 401/02* (2006.01)
*C07D 413/02* (2006.01)
*C07D 417/02* (2006.01)

(52) U.S. Cl. .................. 514/419; 514/414; 514/217.04; 514/228.2; 514/235.2; 514/316; 514/323; 540/597; 544/124; 544/144; 546/187; 546/201; 548/468

(58) Field of Classification Search .................. 514/419, 514/414, 217.04, 228.2, 235.2, 316, 323; 540/597; 544/124, 144; 546/187, 201; 548/468
See application file for complete search history.

(56) References Cited

U.S. PATENT DOCUMENTS

| | | | |
|---|---|---|---|
| 4,598,089 | A | 7/1986 | Hadvary et al. |
| 4,931,463 | A | 6/1990 | Barbier et al. |
| 4,983,746 | A | 1/1991 | Barbier et al. |
| 5,175,186 | A | 12/1992 | Barbier et al. |
| 5,246,960 | A | 9/1993 | Barbier et al. |
| 5,399,720 | A | 3/1995 | Karpf et al. |
| 6,004,996 | A | 12/1999 | Shah et al. |
| 7,361,682 | B2 * | 4/2008 | McArthur et al. ........... 514/419 |
| 7,507,736 | B2 * | 3/2009 | Nettekoven et al. ..... 514/253.04 |
| 7,538,101 | B2 * | 5/2009 | Nettekoven et al. ..... 514/212.01 |

2005/0282864 A1  12/2005  McArthur et al.

FOREIGN PATENT DOCUMENTS

| | | |
|---|---|---|
| EP | 0 189 577 | 12/1989 |
| EP | 0 185 359 | 12/1991 |
| EP | 0 524 495 | 10/1996 |
| EP | 0 443 449 | 5/1997 |
| WO | WO 99/34786 | 7/1999 |
| WO | WO 00/09122 | 2/2000 |
| WO | WO 00/09123 | 2/2000 |
| WO | WO 00/58293 | 10/2000 |
| WO | WO 2005/123716 A1 | 12/2005 |

OTHER PUBLICATIONS

Burks 1994 in Johnson L.R. ed., Physiology of the Gastrointestinal Tract, Raven Press, NY, pp. 211-242.
Leurs et al., Br J. Pharmacol. 1991, 102, pp. 179-185.
Raithel et al., Int. Arch. Allergy Immunol. 1995, 108, 127-133.
Panula et al., Proc. Natl. Acad. Sci. USA 1984, 81, 2572-2576.
Inagaki et al., J. Comp. Neurol 1988, 273, 283-300.
Arrang et al., Nature 1983, 302, 832-837.
Arrang et al., Neuroscience 1987, 23, 149-157.
Clapham & Kilpatrik, Br. J. Pharmacol. 1982, 107, 919-923.
Blandina et al. in The Histamine H3 Receptor (Leurs RL and Timmermann H eds, 1998, pp. 27-40, Elsevier, Amsterdam, The Netherlands.
Masaki et al; Endocrinol. 2003, 144, 2741-2748.
Hancock et al., European J. of Pharmacol. 2004, 487, 183-197.
Timmermann, J. Med. Chem. 1990, 33, 4-11.
Mederski, W. W. K. R.; Lefort, M.; Germann, M. Kux, D. Tetrahedron 1999 55 12757.
Watanabe, M; Nishiyama, M.; Yamamoto, T.; Koie, Y, Tetrahedron Letters 2000, 41, 481.
Old, D. W.; Harris, M. C.; Buchwald, S. L 2000 2 10 1403.

(Continued)

*Primary Examiner*—Rebecca L Anderson
*Assistant Examiner*—Jason M Nolan
(74) *Attorney, Agent, or Firm*—George W. Johnston; Dennis P. Tramaloni; Samuel H. Megerditchian

(57) ABSTRACT

The present invention relates to compounds of formula I

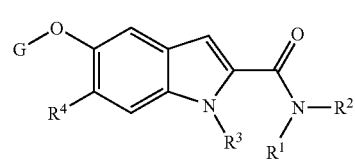

wherein $R^1$ to $R^4$ and G are defined in the description and claims and pharmaceutically acceptable salts thereof. The compounds are useful for the treatment and/or prevention of diseases which are associated with the modulation of H3 receptors.

22 Claims, No Drawings

OTHER PUBLICATIONS

Klapars, A.; Antilla, J. C.; Huang, X.; Buchwald, S. L. J. Am. Chem. Soc. 2001 123 7727.

Takahashi, K, Tokita, S., Kotani, H. (2003) J. Pharmacol. Exp. Therapeutics 307, 213-218.

Cheng, Y, Prusoff, WH (1973) Biochem Pharmacol 22, 3099-3108.

Venable Jennifer, D., et al., Journal of Medicinal Chemistry, vol. 48, No. 26, pp. 8289-8298 (2005), XP002433085.

* cited by examiner

1,5-SUBSTITUTED INDOL-2-YL AMIDE DERIVATIVES

PRIORITY TO RELATED APPLICATIONS

This application claims the benefit of European Application No. 05111478.3, filed Nov. 30, 2005, which is hereby incorporated by reference in its entirety.

FIELD OF THE INVENTION

The present invention is concerned with new 1,5-substituted indol-2-yl amide derivatives, their manufacture, pharmaceutical compositions containing them and their use as medicaments. The active compounds of the present invention are useful in treating obesity and other disorders.

In particular, the present invention relates to compounds of the general formula

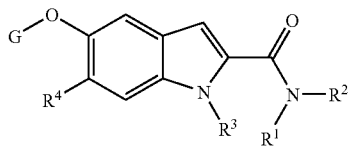

and pharmaceutically acceptable salts thereof.

All documents cited or relied upon below are expressly incorporated herein by reference.

BACKGROUND

The compounds of formula I are antagonists and/or inverse agonists at the histamine 3 receptor (H3 receptor).

Histamine (2-(4-imidazolyl) ethylamine) is one of the aminergic neurotransmitters which is widely distributed throughout the body, e. g. the gastrointestinal tract (Burks 1994 in Johnson L. R. ed., Physiology of the Gastrointestinal Tract, Raven Press, NY, pp. 211-242). Histamine regulates a variety of digestive pathophysiological events like gastric acid secretion, intestinal motility (Leurs et al., Br J. Pharmacol. 1991, 102, pp 179-185), vasomotor responses, intestinal inflammatory responses and allergic reactions (Raithel et al., Int. Arch. Allergy Immunol. 1995, 108, 127-133). In the mammalian brain, histamine is synthesized in histaminergic cell bodies which are found centrally in the tuberomammillary nucleus of the posterior basal hypothalamus. From there, the histaminergic cell bodies project to various brain regions (Panula et al., Proc. Natl. Acad. Sci. USA 1984, 81, 2572-2576; Inagaki et al., J. Comp. Neurol 1988, 273, 283-300).

According to current knowledge, histamine mediates all its actions in both the CNS and the periphery through four distinct histamine receptors, the histamine H1, H2, H3 and H4 receptors.

H3 receptors are predominantly localized in the central nervous system (CNS). As an autoreceptor, H3 receptors constitutively inhibit the synthesis and secretion of histamine from histaminergic neurons (Arrang et al., Nature 1983, 302, 832-837; Arrang et al., Neuroscience 1987, 23, 149-157). As heteroreceptors, H3 receptors also modulate the release of other neurotransmitters such as acetylcholine, dopamine, serotonin and norepinephrine among others in both the central nervous system and in peripheral organs, such as lungs, cardiovascular system and gastrointestinal tract (Clapham & Kilpatrik, Br. J. Pharmacol. 1982, 107, 919-923; Blandina et al. in The Histamine H3 Receptor (Leurs R L and Timmermann H eds, 1998, pp 27-40, Elsevier, Amsterdam, The Netherlands). H3 receptors are constitutively active, meaning that even without exogenous histamine, the receptor is tonically activated. In the case of an inhibitory receptor such as the H3 receptor, this inherent activity causes tonic inhibition of neurotransmitter release. Therefore it may be important that a H3R antagonist would also have inverse agonist activity to both block exogenous histamine effects and to shift the receptor from its constitutively active (inhibitory) form to a neutral state.

The wide distribution of H3 receptors in the mammalian CNS indicates the physiological role of this receptor. Therefore the therapeutic potential as a novel drug development target in various indications has been proposed.

The administration of H3R ligands—as antagonists, inverse agonists, agonists or partial agonists—may influence the histamine levels or the secretion of neurotransmitters in the brain and the periphery and thus may be useful in the treatment of several disorders. Such disorders include obesity (Masaki et al; Endocrinol. 2003, 144, 2741-2748; Hancock et al., European J. of Pharmacol. 2004, 487, 183-197), cardiovascular disorders such as acute myocardial infarction, dementia and cognitive disorders such as attention deficit hyperactivity disorder (ADHD) and Alzheimer's disease, neurological disorders such as schizophrenia, depression, epilepsy, Parkinson's disease and seizures or convulsions, sleep disorders, narcolepsy, pain, gastrointestinal disorders, vestibular dysfunction such as Morbus Meniere, drug abuse and motion sickness (Timmermann, J. Med. Chem. 1990, 33, 4-11).

There is a need, therefore, for selective, directly acting H3 receptor antagonists respectively inverse agonists. Such antagonists/inverse agonists are useful as therapeutically active substances, particularly in the treatment and/or prevention of diseases which are associated with the modulation of H3 receptors.

SUMMARY OF THE INVENTION

In one embodiment of the present invention, provided is a compound of formula I,

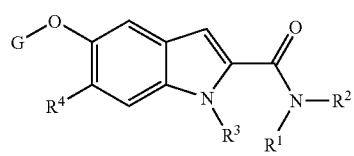

wherein:
R$^1$ is selected from the group consisting of
  lower alkyl, lower alkenyl, lower alkynyl,
  cycloalkyl, lower cycloalkylalkyl,
  lower hydroxyalkyl,
  lower alkoxyalkyl,
  lower alkylsulfanylalkyl,
  lower dialkylaminoalkyl,
  lower dialkylcarbamoylalkyl,
  phenyl unsubstituted or substituted with one or two groups independently selected from lower alkyl, lower halogenoalkoxy and lower hydroxyalkyl, lower phenylalkyl wherein the phenyl ring may be unsubstituted or substituted with one or two groups independently selected from lower alkyl, halogen, lower alkoxy and lower hydroxyalkyl, lower heteroarylalkyl wherein the heteroaryl ring may be unsubstituted or substituted with one or two groups independently selected from lower alkyl, halogen, lower alkoxy and lower hydroxyalkyl and lower heterocyclylalkyl wherein the heterocyclyl ring may be unsubstituted or substituted with one or two lower alkyl groups;

$R^2$ is selected from the group consisting of hydrogen,
lower alkyl, lower alkenyl, lower alkynyl,
cycloalkyl, lower cycloalkylalkyl,
lower hydroxyalkyl, lower alkoxyalkyl,
lower alkylsulfanylalkyl,
lower dialkylaminoalkyl,
lower dialkylcarbamoylalkyl, phenyl unsubstituted or substituted with one or two groups independently selected from lower alkyl, lower halogenoalkoxy and lower hydroxyalkyl, lower phenylalkyl wherein the phenyl ring may be unsubstituted or substituted with one or two groups independently selected from lower alkyl, halogen, lower alkoxy and lower hydroxyalkyl, lower heteroarylalkyl wherein the heteroaryl ring may be unsubstituted or substituted with one or two groups independently selected from lower alkyl, halogen, lower alkoxy and lower hydroxyalkyl and lower heterocyclylalkyl wherein the heterocyclyl ring may be unsubstituted or substituted with one or two lower alkyl groups; or $R^1$ and $R^2$ together with the nitrogen atom to which they are attached form a 4-, 5-, 6- or 7-membered saturated or partly unsaturated heterocyclic ring optionally containing a further heteroatom selected from nitrogen, oxygen or sulfur, said saturated or partly unsaturated heterocyclic ring
being unsubstituted or substituted by one, two or three groups independently selected from lower alkyl, halogen, halogenoalkyl, hydroxy, lower hydroxyalkyl, lower alkoxy, oxo, phenyl, benzyl, pyridyl and carbamoyl, or being condensed with a phenyl ring, said phenyl ring being unsubstituted or substituted by one, two or three groups independently selected from lower alkyl, lower alkoxy and halogen;

$R^3$ is selected from the group consisting of lower hydroxyalkyl,
lower cyanoalkyl, lower alkoxycarbonyl,
phenylsulfonyl wherein the phenyl ring may be unsubstituted or substituted with one or two groups independently selected from lower alkyl, halogen, cyano, lower halogenoalkyl, lower alkoxy, lower halogenoalkoxy and lower hydroxyalkyl;

phenyl unsubstituted or substituted with one or two groups independently selected from lower alkyl, halogen, lower halogenoalkyl, cyano, lower alkoxy, lower halogenoalkoxy and lower hydroxyalkyl;

lower phenylalkyl, wherein the phenyl ring may be unsubstituted or substituted with one or two groups independently selected from lower alkyl, halogen, lower halogenoalkyl, cyano, lower alkoxy, lower halogenoalkoxy and lower hydroxyalkyl; and heteroaryl unsubstituted or substituted with one or two groups independently selected from lower alkyl, lower alkoxy, halogen, lower halogenoalkyl, lower halogenoalkoxy, morpholino and cyano;

$R^4$ is hydrogen or halogen;
G is a group selected from

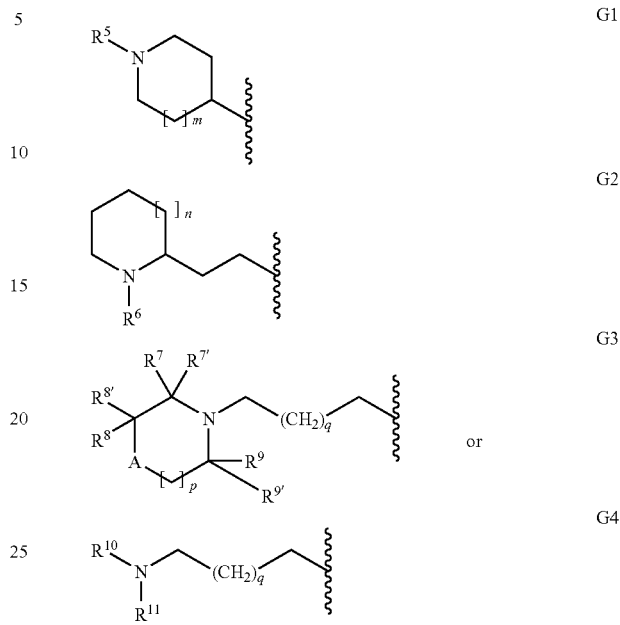

wherein
m is 0, 1 or 2;
$R^5$ is selected from lower alkyl, lower halogenoalkyl, cycloalkyl, halogenocycloalkyl, lower cycloalkylalkyl and lower phenylalkyl;
n is 0, 1 or 2;
$R^6$ is lower alkyl;
p is 0, 1 or 2;
q is 0, 1 or 2;
A is selected from $CR^{12}R^{12'}$, O and S;
$R^7$, $R^{7'}$, $R^8$, $R^{8'}$, $R^9$, $R^{9'}$, $R^{12}$ and $R^{12'}$ independently from each other are selected from the group consisting of hydrogen, lower alkyl, hydoxy, halogen and dialkylamino, or
$R^8$ and $R^{12}$ together form a double bond;
$R^{10}$ is lower alkyl;
$R^{11}$ is $C_3$-$C_6$-alkyl;

and pharmaceutically acceptable salts thereof.

In another embodiment of the present invention, provided is a process for the manufacture of compounds according to formula I, comprising the steps of: treating a compound of the formula II

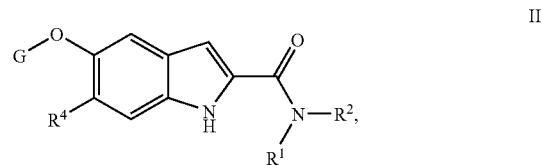

wherein $R^1$, $R^2$ and $R^4$ are as defined for formula I, with a suitable base in a suitable solvent under anhydrous conditions and reacting the intermediate anion with an alkylating or acylating agent of the formula III $$R^3\text{—}X \qquad \text{III,}$$

wherein X signifies a leaving group and $R^3$ is selected from the group consisting of lower hydroxyalkyl, lower cyanoalkyl, optionally substituted lower phenylalkyl, lower alkoxycarbonyl and optionally substituted phenylsulfonyl,

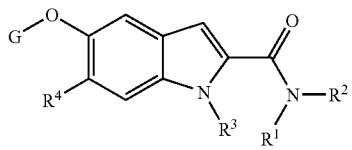

Ia wherein $R^3$ is selected from the group consisting of lower hydroxyalkyl, lower cyanoalkyl, optionally substituted lower phenylalkyl, lower alkoxycarbonyl and optionally substituted phenylsulfonyl,
and if desired,
converting the compound obtained into a pharmaceutically acceptable acid addition salt, or alternatively,
reacting a compound of formula II

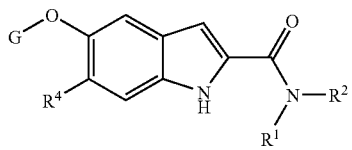

II wherein $R^1$, $R^2$ and $R^4$ are as defined for formula I, with an optionally substituted phenyl- or heteroaryl boronic acid of the formula IV

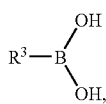

IV wherein $R^3$ signifies optionally substituted aryl or heteroaryl, in the presence of a catalyst and basic conditions to obtain a compound of the formula

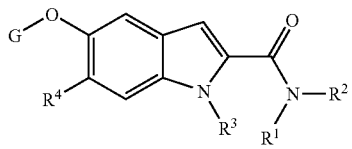

Ib wherein $R^3$ signifies optionally substituted aryl or optionally substituted heteroaryl, and if desired,
converting the compound obtained into a pharmaceutically acceptable acid addition salt.

In a further embodiment of the present invention, provided is a pharmaceutical composition, comprising a therapeutically effective amount of a compound according to formula I and a pharmaceutically acceptable carrier and/or adjuvant.

In another embodiment of the present invention, provided is a method for the treatment and/or prevention of diseases which are associated with the modulation of H3 receptors, comprising the step of administering a therapeutically effective amount of a compound according to formula I to a human being or animal in need thereof.

In a yet still further embodiment of the present invention, provided is a method for the treatment or prevention of obesity in a human being or animal, comprising the step of administering a therapeutically effective amount of a compound according to formula I in combination or association with a therapeutically effective amount of a compound selected from the group consisting of a lipase inhibitor, an anorectic agent, a selective serotonin reuptake inhibitor and an agent that stimulates metabolism of body fat, to said human being or animal in need thereof.

In a yet still another embodiment of the present invention, provided is a method of treatment or prevention of type II diabetes in a human being or animal, comprising the step of administering a therapeutically effective amount of a compound according to formula I in combination or association with a therapeutically effective amount of an anti-diabetic agent to said human being or animal in need thereof.

DETAILED DESCRIPTION

In the present description the term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms.

The term "lower alkyl" or "$C_1$-$C_8$-alkyl", alone or in combination, signifies a straight-chain or branched-chain alkyl group with 1 to 8 carbon atoms, preferably a straight or branched-chain alkyl group with 1 to 6 carbon atoms and particularly preferred a straight or branched-chain alkyl group with 1 to 4 carbon atoms. Examples of straight-chain and branched $C_1$-$C_8$ alkyl groups are methyl, ethyl, propyl, isopropyl, butyl, isobutyl, tert.-butyl, the isomeric pentyls, the isomeric hexyls, the isomeric heptyls and the isomeric octyls, preferably methyl and ethyl and most preferred methyl.

The term "lower alkenyl" or "$C_{2-8}$-alkenyl", alone or in combination, signifies a straight-chain or branched hydrocarbon radical comprising an olefinic bond and up to 8, preferably up to 6, particularly preferred up to 4 carbon atoms. Examples of alkenyl groups are ethenyl, 1-propenyl, 2-propenyl, isopropenyl, 1-butenyl, 2-butenyl, 3-butenyl and isobutenyl. A preferred example is 2-propenyl.

The term "lower alkynyl" or "$C_{2-8}$-alkynyl", alone or in combination, signifies a straight-chain or branched hydrocarbon residue comprising a triple bond and up to 8, preferably up to 6, particularly preferred up to 4 carbon atoms. Examples of alkynyl groups are ethinyl, 1-propinyl, or 2-propinyl. A preferred example is 2-propinyl.

The term "cycloalkyl" or "$C_{3-7}$-cycloalkyl" denotes a saturated carbocyclic group containing from 3 to 7 carbon atoms, such as cyclopropyl, cyclobutyl, cyclopentyl, cyclohexyl or cycloheptyl.

Especially preferred are cyclopropyl, cyclopentyl and cyclohexyl.

The term "lower cycloalkylalkyl" or "$C_{3-7}$-cycloalkyl-$C_{1-8}$-alkyl" refers to lower alkyl groups as defined above wherein at least one of the hydrogen atoms of the lower alkyl group is replaced by cycloalkyl. A preferred example is cyclopropylmethyl.

The term "alkoxy" refers to the group R'—O—, wherein R' is lower alkyl and the term "lower alkyl" has the previously given significance. Examples of lower alkoxy groups are e.g. methoxy, ethoxy, n-propoxy, isopropoxy, n-butoxy, isobutoxy, sec. butoxy and tert.-butoxy, preferably methoxy and ethoxy and most preferred methoxy.

The term "lower alkoxyalkyl" or "$C_{1-8}$-alkoxy-$C_{1-8}$-alkyl" refers to lower alkyl groups as defined above wherein at least one of the hydrogen atoms of the lower alkyl groups is replaced by an alkoxy group, preferably methoxy or ethoxy. Among the preferred lower alkoxyalkyl groups are 2-methoxyethyl or 3-methoxypropyl.

The term "alkylsulfanyl" or "$C_{1-8}$-alkylsulfanyl" refers to the group R'—S—, wherein R' is lower alkyl and the term "lower alkyl" has the previously given significance. Examples of alkylsulfanyl groups are e.g. methylsulfanyl or ethylsulfanyl.

The term "lower alkylsulfanylalkyl" or "$C_{1-8}$-alkylsulfanyl-$C_{1-8}$-alkyl" refers to lower alkyl groups as defined above wherein at least one of the hydrogen atoms of the lower alkyl groups is replaced by an alkylsulfanyl group, preferably methylsulfanyl. An example for a preferred lower alkylsulfanylalkyl group is 2-methylsulfanylethyl.

The term "alkylsulfonyl" or "lower alkylsulfonyl" refers to the group R'—S(O)$_2$—, wherein R' is lower alkyl and the term "lower alkyl" has the previously given significance. Examples of alkylsulfonyl groups are e.g. methylsulfonyl or ethylsulfonyl.

The term "halogen" refers to fluorine, chlorine, bromine and iodine, with fluorine, chlorine and bromine being preferred.

The term "lower halogenoalkyl" or "halogen-$C_{1-8}$-alkyl" refers to lower alkyl groups as defined above wherein at least one of the hydrogen atoms of the lower alkyl group is replaced by a halogen atom, preferably fluoro or chloro, most preferably fluoro. Among the preferred halogenated lower alkyl groups are trifluoromethyl, difluoromethyl, fluoromethyl and chloromethyl, with trifluoromethyl being especially preferred.

The term "lower halogenoalkoxy" or "halogen-$C_{1-8}$-alkoxy" refers to lower alkoxy groups as defined above wherein at least one of the hydrogen atoms of the lower alkoxy group is replaced by a halogen atom, preferably fluoro or chloro, most preferably fluoro. Among the preferred halogenated lower alkyl groups are trifluoromethoxy, difluoromethoxy, fluormethoxy and chloromethoxy, with trifluoromethoxy being especially preferred.

The term "lower hydroxyalkyl" or "hydroxy-$C_{1-8}$-alkyl" refers to lower alkyl groups as defined above wherein at least one of the hydrogen atoms of the lower alkyl group is replaced by a hydroxy group. Examples of lower hydroxyalkyl groups are hydroxymethyl or hydroxyethyl.

The term "dialkylamino" refers to the group —NR'R", wherein R' and R" are lower alkyl and the term "lower alkyl" has the previously given significance. A preferred dialkylamino group is dimethylamino.

The term "lower dialkylaminoalkyl" or "$C_{1-8}$-dialkylamino-$C_{1-8}$-alkyl" refers to lower alkyl groups as defined above wherein at least one of the hydrogen atoms of the lower alkyl group is replaced by a dialkylamino group, preferably dimethylamino. A preferred lower dialkylaminoalkyl group is 3-dimethylaminopropyl.

The term "lower alkanoyl" refers to the group —CO—R', wherein R' is lower alkyl and the term "lower alkyl" has the previously given significance. Preferred is a group —CO—R', wherein R' is methyl, meaning an acetyl group.

The term "lower alkoxycarbonyl" or "$C_{1-8}$-alkoxycarbonyl" refers to the group —COOR', wherein R' is lower alkyl and the term "lower alkyl" has the previously given significance. Preferred is a group —COOR', wherein R' is methyl.

The term "carbamoyl" refers to the group —CO—NH$_2$.

The term "dialkylcarbamoyl" or "$C_{1-8}$-dialkylcarbamoyl" refers to the group —CO—NR'R" wherein R' and R" are lower alkyl and the term "lower alkyl" has the previously given significance. A preferred dialkylcarbamoyl group is dimethylcarbamoyl.

The term "lower dialkylcarbamoylalkyl" or "$C_{1-8}$-dialkylcarbamoyl-$C_{1-8}$-alkyl" refers to lower alkyl groups as defined above wherein at least one of the hydrogen atoms of the lower alkyl group is replaced by a dialkylcarbamoyl group as defined herein before. A preferred lower dialkylcarbamoylalkyl groups is dimethylcarbamoylmethyl.

The term "lower phenylalkyl" or "phenyl-$C_{1-8}$-alkyl" to lower alkyl groups as defined above wherein at least one of the hydrogen atoms of the lower alkyl group is replaced by a phenyl group. Preferred lower phenylalkyl groups are benzyl or phenethyl.

The term "heteroaryl" refers to an aromatic 5- or 6-membered ring which can comprise one, two or three atoms selected from nitrogen, oxygen and/or sulphur. Examples of heteroaryl groups are e.g. furyl, pyridyl, pyrazinyl, pyrimidinyl, pyridazinyl, thienyl, isoxazolyl, thiazolyl, isothiazolyl, oxazolyl, imidazolyl, or pyrrolyl. Especially preferred are furyl, thienyl, pyrimidyl and pyridyl.

Most preferred are furyl and pyridyl.

The term "lower heteroarylalkyl" or "heteroaryl-$C_{1-8}$-alkyl" refers to lower alkyl groups as defined above wherein at least one of the hydrogen atoms of the lower alkyl group is replaced by a heteroaryl group as defined above.

The term "heterocyclyl" refers to a saturated or partly unsaturated 5- or 6-membered ring which can comprise one, two or three atoms selected from nitrogen, oxygen and/or sulphur. Examples of heterocyclyl rings include piperidinyl, piperazinyl, azepinyl, pyrrolidinyl, pyrazolidinyl, imidazolinyl, imidazolidinyl, pyridinyl, pyridazinyl, pyrimidinyl, oxazolidinyl, isoxazolidinyl, morpholinyl, thiazolidinyl, isothiazolidinyl, thiadiazolylidinyl, dihydrofuryl, tetrahydrofuryl, dihydropyranyl, tetrahydropyranyland thiomorpholinyl. A preferred heterocyclyl group is piperidinyl.

The term "lower heterocyclylalkyl" or "heterocyclyl-$C_{1-8}$-alkyl" refers to lower alkyl groups as defined above wherein at least one of the hydrogen atoms of the lower alkyl group is replaced by a heterocyclyl group as defined above.

The term "form a 4-, 5-, 6- or 7-membered saturated heterocyclic ring optionally containing a further heteroatom selected from nitrogen, oxygen or sulfur" refers to a saturated N-heterocyclic ring, which may optionally contain a further nitrogen, oxygen or sulfur atom, such as azetidinyl, pyrrolidinyl, imidazolidinyl, pyrazolidinyl, oxazolidinyl, isoxazolidinyl, thiazolidinyl, isothiazolidinyl, piperidinyl, piperazinyl, morpholinyl, thiomorpholinyl, or azepanyl. A "4-, 5-, 6- or 7-membered partly unsaturated heterocyclic ring" means a heterocyclic ring as defined above which contains a double bond, for example 2,5-dihydropyrrolyl or 3,6-dihydro-2H-pyridinyl. The heterocyclic ring may be unsubstituted or substituted by one, two or three groups independently selected from lower alkyl, lower alkoxy and oxo. The heterocyclic ring may also be condensed with a phenyl ring, said phenyl ring being unsubstituted or substituted by one, two or three groups independently selected from lower alkyl, lower alkoxy and halogen. An example for such a condensed heterocyclic ring is 3,4-dihydro-1H-isoquinoline.

The term "oxo" means that a C-atom of the heterocyclic ring may be substituted by =O, thus meaning that the heterocyclic ring may contain one or more carbonyl (—CO—) groups.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, preferably hydrochloric acid and organic acids such as acetic acid, propionic acid, glycolic acid, pyruvic acid, oxylic acid, maleic acid, malonic acid, salicylic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared form addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polymine resins and the like. The compound of formula I can also be present in the form of zwitterions. Particularly preferred pharmaceutically acceptable salts of compounds of formula I are the hydrochloride salts.

The compounds of formula I can also be solvated, e.g. hydrated. The solvation can be effected in the course of the manufacturing process or can take place e.g. as a consequence of hygroscopic properties of an initially anhydrous compound of formula I (hydration). The term pharmaceutically acceptable salts also includes physiologically acceptable solvates.

"Isomers" are compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers" and stereoisomers that are non-superimposable mirror images are termed "enantiomers", or sometimes optical isomers. A carbon atom bonded to four nonidentical substituents is termed a "chiral center".

In detail, the present invention relates to compounds of the general formula

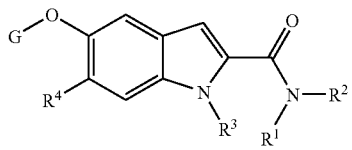

I wherein
R$^1$ is selected from the group consisting of
  lower alkyl, lower alkenyl, lower alkynyl,
  cycloalkyl, lower cycloalkylalkyl,
  lower hydroxyalkyl,
  lower alkoxyalkyl,
  lower alkylsulfanylalkyl,
  lower dialkylaminoalkyl,
  lower dialkylcarbamoylalkyl,
  phenyl unsubstituted or substituted with one or two groups independently selected from lower alkyl, lower halogenoalkoxy and lower hydroxyalkyl, lower phenylalkyl wherein the phenyl ring may be unsubstituted or substituted with one or two groups independently selected from lower alkyl, halogen, lower alkoxy and lower hydroxyalkyl,
  lower heteroarylalkyl wherein the heteroaryl ring may be unsubstituted or substituted with one or two groups independently selected from lower alkyl, halogen, lower alkoxy and lower hydroxyalkyl and
  lower heterocyclylalkyl wherein the heterocyclyl ring may be unsubstituted or substituted with one or two lower alkyl groups;
R$^2$ is selected from the group consisting of hydrogen,
  lower alkyl, lower alkenyl, lower alkynyl,
  cycloalkyl, lower cycloalkylalkyl,
  lower hydroxyalkyl, lower alkoxyalkyl,
  lower alkylsulfanylalkyl,
  lower dialkylaminoalkyl,
  lower dialkylcarbamoylalkyl,
  phenyl unsubstituted or substituted with one or two groups independently selected from lower alkyl, lower halogenoalkoxy and lower hydroxyalkyl, lower phenylalkyl wherein the phenyl ring may be unsubstituted or substituted with one or two groups independently selected from lower alkyl, halogen, lower alkoxy and lower hydroxyalkyl,
  lower heteroarylalkyl wherein the heteroaryl ring may be unsubstituted or substituted with one or two groups independently selected from lower alkyl, halogen, lower alkoxy and lower hydroxyalkyl and
  lower heterocyclylalkyl wherein the heterocyclyl ring may be unsubstituted or substituted with one or two lower alkyl groups; or
R$^1$ and R$^2$ together with the nitrogen atom to which they are attached form a 4-, 5-, 6- or 7-membered saturated or partly unsaturated heterocyclic ring optionally containing a further heteroatom selected from nitrogen, oxygen or sulfur, said saturated or partly unsaturated heterocyclic ring being unsubstituted or substituted by one, two or three groups independently selected from lower alkyl, halogen, halogenoalkyl, hydroxy, lower hydroxyalkyl, lower alkoxy, oxo, phenyl, benzyl, pyridyl and carbamoyl, or being condensed with a phenyl ring, said phenyl ring being unsubstituted or substituted by one, two or three groups independently selected from lower alkyl, lower alkoxy and halogen;
R$^3$ is selected from the group consisting of lower hydroxyalkyl, lower cyanoalkyl, lower alkoxycarbonyl,
  phenylsulfonyl wherein the phenyl ring may be unsubstituted or substituted with one or two groups independently selected from lower alkyl, halogen, cyano, lower halogenoalkyl, lower alkoxy, lower halogenoalkoxy and lower hydroxyalkyl;
  phenyl unsubstituted or substituted with one or two groups independently selected from lower alkyl, halogen, lower halogenoalkyl, cyano, lower alkoxy, lower halogenoalkoxy and lower hydroxyalkyl;
  lower phenylalkyl, wherein the phenyl ring may be unsubstituted or substituted with one or two groups independently selected from lower alkyl, halogen, lower halogenoalkyl, cyano, lower alkoxy, lower halogenoalkoxy and lower hydroxyalkyl; and heteroaryl unsubstituted or substituted with one or two groups independently selected from lower alkyl, lower alkoxy, halogen, lower halogenoalkyl, lower halogenoalkoxy, morpholino and cyano;

$R^4$ is hydrogen or halogen;

G is a group selected from

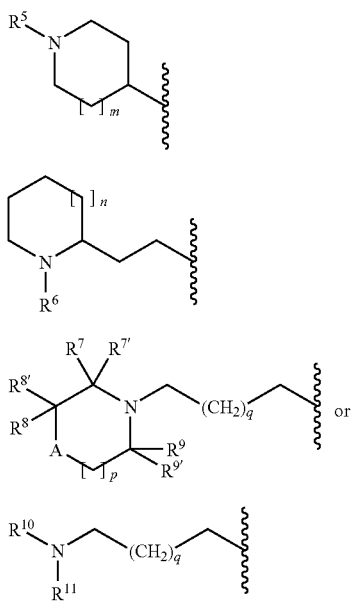

wherein m is 0, 1 or 2;

$R^5$ is selected from lower alkyl, lower halogenoalkyl, cycloalkyl, halogenocycloalkyl, lower cycloalkylalkyl and lower phenylalkyl;

n is 0, 1 or 2;

$R^6$ is lower alkyl;

p is 0, 1 or 2;

q is 0, 1 or 2;

A is selected from $CR^{12}R^{12'}$, O and S;

$R^7, R^{7'}, R^8, R^{8'}, R^9, R^{9'}, R^{12}$ and $R^{12'}$ independently from each other are selected from the group consisting of hydrogen, lower alkyl, hydoxy, halogen and dialkylamino, or $R^8$ and $R^{12}$ together form a double bond;

$R^{10}$ is lower alkyl;

$R^{11}$ is $C_3$-$C_6$-alkyl;

and pharmaceutically acceptable salts thereof.

Preferred are compounds of formula I according to the present invention, wherein $R^1$ and $R^2$ together with the nitrogen atom to which they are attached form a 4-, 5-, 6- or 7-membered saturated or partly unsaturated heterocyclic ring optionally containing a further heteroatom selected from nitrogen, oxygen or sulfur, said saturated or partly unsaturated heterocyclic ring being unsubstituted or substituted by one, two or three groups independently selected from lower alkyl, halogen, halogenoalkyl, hydroxy, lower hydroxyalkyl, lower alkoxy, oxo, phenyl, benzyl, pyridyl and carbamoyl, or being condensed with a phenyl ring, said phenyl ring being unsubstituted or substituted by one, two or three groups independently selected from lower alkyl, lower alkoxy and halogen.

More preferred are compounds of formula I according to the invention, wherein $R^1$ and $R^1$ together with the nitrogen atom to which they are attached form a heterocyclic ring selected from the group consisting of morpholine, piperidine, 2,5-dihydropyrrole, pyrrolidine, azepane, piperazine, azetidine, thiomorpholine and 3,6-dihydro-2H-pyridine, said heterocyclic ring being unsubstituted or substituted by one, two or three groups independently selected from lower alkyl, halogen, halogenoalkyl, hydroxy, lower alkoxy, oxo, phenyl, benzyl, pyridyl and carbamoyl, or being condensed with a phenyl ring, said phenyl ring being unsubstituted or substituted by one, two or three groups independently selected from lower alkyl, lower alkoxy and halogen.

Even more preferably, $R^1$ and $R^2$ together with the nitrogen atom to which they are attached form a heterocyclic ring selected from the group consisting of morpholine, piperidine, 4-hydroxy-4-methylpiperidine, 4,4-difluoropiperidine and pyrrolidine.

Most preferably, $R^1$ and $R^2$ together with the nitrogen atom to which they are attached form a morpholine or 4,4-difluoropiperidine ring.

Preferred compounds of formula I of the present invention are also compounds of formula I, wherein $R^1$ is selected from the group consisting of
lower alkyl, lower alkenyl, lower alkynyl,
cycloalkyl, lower cycloalkylalkyl,
lower hydroxyalkyl, lower alkoxyalkyl,
lower alkylsulfanylalkyl,
lower dialkylaminoalkyl, lower dialkylcarbamoylalkyl,
phenyl unsubstituted or substituted with one or two groups independently selected from lower alkyl, lower halogenoalkoxy or lower hydroxyalkyl,
lower phenylalkyl wherein the phenyl ring may be unsubstituted or substituted with one or two groups independently selected from lower alkyl, halogen, lower alkoxy or lower hydroxyalkyl,
lower heteroarylalkyl wherein the heteroaryl ring may be unsubstituted or substituted with one or two groups independently selected from lower alkyl, halogen, lower alkoxy or lower hydroxyalkyl and
lower heterocyclylalkyl wherein the heterocyclyl ring may be unsubstituted or substituted with one or two lower alkyl groups and $R^2$ is hydrogen or lower alkyl.

More preferred are compounds of formula I, wherein
$R^1$ is selected from the group consisting of
lower alkyl,
cycloalkyl, lower cycloalkylalkyl,
lower alkoxyalkyl and
lower phenylalkyl wherein the phenyl ring may be unsubstituted or substituted with one or two groups independently selected from lower alkyl, halogen, lower alkoxy or lower hydroxyalkyl and
$R^2$ is hydrogen or lower alkyl.

Especially preferred are those compounds of formula I, wherein $R^1$ is lower phenylalkyl wherein the phenyl ring may be unsubstituted or substituted with one or two groups independently selected from lower alkyl, halogen, lower alkoxy or lower hydroxyalkyl and $R^2$ is hydrogen or lower alkyl.

Also preferred are compounds of formula I, wherein $R^1$ and $R^2$ are lower alkyl.

Compounds of the present invention are further compounds of formula I, wherein $R^3$ is selected from the group consisting of lower hydroxyalkyl, lower cyanoalkyl, lower alkoxycarbonyl,
phenylsulfonyl wherein the phenyl ring may be unsubstituted or substituted with one or two groups independently selected from lower alkyl, halogen, cyano, lower halogenoalkyl, lower alkoxy, lower halogenoalkoxy and lower hydroxyalkyl;

phenyl unsubstituted or substituted with one or two groups independently selected from lower alkyl, halogen, lower halogenoalkyl, cyano, lower alkoxy, lower halogenoalkoxy and lower hydroxyalkyl;

lower phenylalkyl, wherein the phenyl ring may be unsubstituted or substituted with one or two groups independently selected from lower alkyl, halogen, lower halogenoalkyl, cyano, lower alkoxy, lower halogenoalkoxy and lower hydroxyalkyl; and heteroaryl unsubstituted or substituted with one or two groups independently selected from lower alkyl, lower alkoxy, halogen, lower halogenoalkyl, lower halogenoalkoxy and cyano.

Furthermore, compounds of formula I according to the present invention are preferred, wherein $R^3$ is selected from the group consisting of lower cyanoalkyl, lower alkoxycarbonyl, phenylsulfonyl, wherein the phenyl ring may be unsubstituted or substituted with one or two groups independently selected from lower alkyl, halogen, cyano, lower halogenoalkyl, lower alkoxy, lower halogenoalkoxy and lower hydroxyalkyl;

phenyl unsubstituted or substituted with one or two groups independently selected from lower alkyl, halogen, lower halogenoalkyl, cyano, lower alkoxy, lower halogenoalkoxy and lower hydroxyalkyl;

lower phenylalkyl, wherein the phenyl ring may be unsubstituted or substituted with one or two groups independently selected from lower alkyl, halogen, lower halogenoalkyl, cyano, lower alkoxy, lower halogenoalkoxy and lower hydroxyalkyl; and heteroaryl unsubstituted or substituted with one or two groups independently selected from lower alkyl, lower alkoxy, halogen, lower halogenoalkyl, lower halogenoalkoxy and cyano.

Especially preferred are compounds of formula I according the invention, wherein $R^3$ is lower cyanoalkyl or lower alkoxycarbonyl.

Also preferred are compounds of formula I, wherein $R^3$ is phenylsulfonyl, wherein the phenyl ring may be unsubstituted or substituted with one or two groups independently selected from lower alkyl, halogen, cyano, lower halogenoalkyl, lower alkoxy, lower halogenoalkoxy and lower hydroxyalkyl.

Further preferred compounds of the present invention are those, wherein $R^3$ is lower phenylalkyl, wherein the phenyl ring may be unsubstituted or substituted with one or two groups independently selected from lower alkyl, halogen, lower halogenoalkyl, cyano, lower alkoxy, lower halogenoalkoxy and lower hydroxyalkyl.

Compounds of formula I, wherein $R^3$ is phenyl unsubstituted or substituted with one or two groups independently selected from lower alkyl, halogen, lower halogenoalkyl, cyano, lower alkoxy, lower halogenoalkoxy and lower hydroxyalkyl, are also preferred, with those compounds, wherein phenyl is substituted by halogen, lower alkoxy or cyano, being especially preferred.

Furthermore, compounds of formula I according to the invention are preferred, wherein $R^3$ is heteroaryl unsubstituted or substituted with one or two groups independently selected from lower alkyl, lower alkoxy, halogen, lower halogenoalkyl, lower halogenoalkoxy and cyano, with those compounds of formula I, wherein heteroaryl is selected from the group consisting of pyridyl, pyrimidinyl, furanyl and thienyl, being especially preferred.

$R^4$ is hydrogen or halogen. Compounds of formula I, wherein $R^4$ is selected from the group consisting of hydrogen, chloro and bromo, are preferred.

Especially preferred compounds of formula I according to the invention are those, wherein $R^4$ is hydrogen.

In addition, compounds of formula I according to the invention are preferred, wherein G signifies

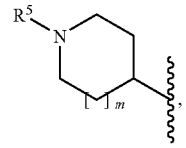

G1 wherein m is 0, 1 or 2 and $R^5$ is selected from lower alkyl, lower halogenoalkyl, cycloalkyl, halogenocycloalkyl, lower cycloalkylalkyl and lower phenylalkyl.

Within this group, those compounds of formula I are preferred, wherein $R^5$ is lower alkyl.

Further preferred compounds of formula I according to the present invention are those compounds, wherein G signifies

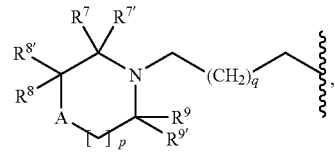

G3 wherein p is 0, 1 or 2, q is 0, 1 or 2, A is selected from $CR^{12}R^{12'}$, O and S and $R^7$, $R^{7'}$, $R^8$, $R^{8'}$, $R^9$, $R^{9'}$, $R^{12}$ and $R^{12'}$ independently from each other are selected from the group consisting of hydrogen, lower alkyl, hydoxy, halogen and dialkylamino, or $R^8$ and $R^{12}$ together form a double bond.

Within this group, those compounds of formula I are especially preferred, wherein A is $CR^{12}R^{12'}$, p is 0, q is 1 and $R^7$, $R^{7'}$, $R^8$, $R^{8'}$, $R^9$, $R^{9'}$, $R^{12}$ and $R^{12'}$ independently from each other are selected from hydrogen or lower alkyl.

Also preferred are compounds of formula I, wherein G signifies

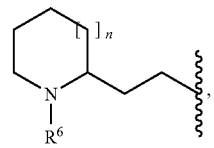

G2 wherein n is 0, 1 or 2 and $R^6$ is lower alkyl.

Compounds of formula I according to the present invention, wherein G signifies

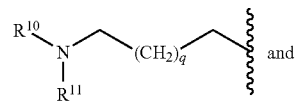

G4 and wherein q is 0, 1 or 2, $R^{10}$ is lower alkyl and $R^{11}$ is lower alkyl, are also preferred.

Particularly preferred compounds of formula I of the present invention are the following:

(4,4-difluoro-piperidin-1-yl)-[1-(4-fluoro-benzenesulfonyl)-5-(1-isopropyl-piperidin-4-yloxy)-1H-indol-2-yl]-methanone,
[1-benzyl-5-(1-isopropyl-piperidin-4-yloxy)-1H-indol-2-yl]-morpholin-4-yl-methanone,
(4,4-difluoro-piperidin-1-yl)-[1-(4-fluoro-benzyl)-5-(1-isopropyl-piperidin-4-yloxy)-1H-indol-2-yl]-methanone,
2-(4,4-difluoro-piperidine-1-carbonyl)-5-(1-isopropyl-piperidin-4-yloxy)-indole-1-carboxylic acid methyl ester,
[2-(4,4-difluoro-piperidine-1-carbonyl)-5-(1-isopropyl-piperidin-4-yloxy)-indol-1-yl]-acetonitrile,
[1-(3,5-difluoro-phenyl)-5-(1-isopropyl-piperidin-4-yloxy)-1H-indol-2-yl]-(4,4-difluoro-piperidin-1-yl)-methanone,
(4,4-difluoro-piperidin-1-yl)-[5-(1-isopropyl-piperidin-4-yloxy)-1-(3-trifluoromethoxy-phenyl)-1H-indol-2-yl]-methanone,
(4,4-difluoro-piperidin-1-yl)-[5-(1-isopropyl-piperidin-4-yloxy)-1-(4-trifluoromethoxy-phenyl)-1H-indol-2-yl]-methanone,
[1-(2-chloro-pyridin-4-yl)-5-(1-isopropyl-piperidin-4-yloxy)-1H-indol-2-yl]-(4,4-difluoro-piperidin-1-yl)-methanone,
[1-(6-chloro-pyridin-3-yl)-5-(1-isopropyl-piperidin-4-yloxy)-1H-indol-2-yl]-(4,4-difluoro-piperidin-1-yl)-methanone,
(4,4-difluoro-piperidin-1-yl)-[5-(1-isopropyl-piperidin-4-yloxy)-1-(2-methoxy-phenyl)-1H-indol-2-yl]-methanone,
(4,4-difluoro-piperidin-1-yl)-[1-(4-fluoro-phenyl)-5-(1-isopropyl-piperidin-4-yloxy)-1H-indol-2-yl]-methanone,
(4,4-difluoro-piperidin-1-yl)-[1-(3-fluoro-phenyl)-5-(1-isopropyl-piperidin-4-yloxy)-1H-indol-2-yl]-methanone,
[1-(3-chloro-phenyl)-5-(1-isopropyl-piperidin-4-yloxy)-1H-indol-2-yl]-(4,4-difluoro-piperidin-1-yl)-methanone,
(4,4-difluoro-piperidin-1-yl)-[5-(1-isopropyl-piperidin-4-yloxy)-1-(3-methoxy-phenyl)-1H-indol-2-yl]-methanone,
(4,4-difluoro-piperidin-1-yl)-[5-(1-isopropyl-piperidin-4-yloxy)-1-(4-trifluoromethyl-phenyl)-1H-indol-2-yl]-methanone,
(4,4-difluoro-piperidin-1-yl)-[5-(1-isopropyl-piperidin-4-yloxy)-1-phenyl-1H-indol-2-yl]-methanone,
(4,4-difluoro-piperidin-1-yl)-[5-(1-isopropyl-piperidin-4-yloxy)-1-p-tolyl-1H-indol-2-yl]-methanone,
[1-(4-chloro-phenyl)-5-(1-isopropyl-piperidin-4-yloxy)-1H-indol-2-yl]-(4,4-difluoro-piperidin-1-yl)-methanone
[1-(3,4-dichloro-phenyl)-5-(1-isopropyl-piperidin-4-yloxy)-1H-indol-2-yl]-(4,4-difluoro-piperidin-1-yl)-methanone,
5-[2-(4,4-difluoro-piperidine-1-carbonyl)-5-(1-isopropyl-piperidin-4-yloxy)-indol-1-yl]-pyridine-2-carbonitrile,
(4,4-difluoro-piperidin-1-yl)-[5-(1-isopropyl-piperidin-4-yloxy)-1-(4-methoxy-phenyl)-1H-indol-2-yl]-methanone,
3-[2-(4,4-difluoro-piperidine-1-carbonyl)-5-(1-isopropyl-piperidin-4-yloxy)-indol-1-yl]-benzonitrile,
4-[2-(4,4-difluoro-piperidine-1-carbonyl)-5-(1-isopropyl-piperidin-4-yloxy)-indol-1-yl]-benzonitrile,
[5-(1-isopropyl-piperidin-4-yloxy)-1-phenyl-1H-indol-2-yl]-morpholin-4-yl-methanone,
[1-(4-chloro-phenyl)-5-(1-isopropyl-piperidin-4-yloxy)-1H-indol-2-yl]-morpholin-4-yl-methanone,
[1-(3,4-dichloro-phenyl)-5-(1-isopropyl-piperidin-4-yloxy)-1H-indol-2-yl]-morpholin-4-yl-methanone,
[5-(1-isopropyl-piperidin-4-yloxy)-1-p-tolyl-1H-indol-2-yl]-morpholin-4-yl-methanone,
[5-(1-isopropyl-piperidin-4-yloxy)-1-(4-methoxy-phenyl)-1H-indol-2-yl]-morpholin-4-yl-methanone,
4-[5-(1-isopropyl-piperidin-4-yloxy)-2-(morpholine-4-carbonyl)-indol-1-yl]-benzonitrile,
5-[2-(4,4-difluoro-piperidine-1-carbonyl)-5-(1-isopropyl-piperidin-4-yloxy)-indol-1-yl]-2-fluoro-benzonitrile,
(4,4-difluoro-piperidin-1-yl)-[5-(1-isopropyl-piperidin-4-yloxy)-1-(2-methoxy-pyrimidin-5-yl)-1H-indol-2-yl]-methanone,
4,4-difluoro-piperidin-1-yl)-[5-(1-isopropyl-piperidin-4-yloxy)-1-thiophen-3-yl-1H-indol-2-yl]-methanone,
(4,4-difluoro-piperidin-1-yl)-[5-(1-isopropyl-piperidin-4-yloxy)-1-pyrimidin-5-yl-1H-indol-2-yl]-methanone,
(4,4-difluoro-piperidin-1-yl)-[5-(1-isopropyl-piperidin-4-yloxy)-1-pyridin-2-yl-1H-indol-2-yl]-methanone,
(4,4-difluoro-piperidin-1-yl)-[5-(1-isopropyl-piperidin-4-yloxy)-1-thiophen-2-yl-1H-indol-2-yl]-methanone,
(4,4-difluoro-piperidin-1-yl)-[5-(1-isopropyl-piperidin-4-yloxy)-1-(6-morpholin-4-yl-pyridin-3-yl)-1H-indol-2-yl]-methanone,
(4,4-difluoro-piperidin-1-yl)-[5-(1-isopropyl-piperidin-4-yloxy)-1-pyridin-3-yl-1H-indol-2-yl]-methanone,
[6-chloro-5-(1-isopropyl-piperidin-4-yloxy)-1-pyrimidin-5-yl-1H-indol-2-yl]-(4,4-difluoro-piperidin-1-yl)-methanone,
[6-chloro-5-(1-isopropyl-piperidin-4-yloxy)-1-pyrimidin-5-yl-1H-indol-2-yl]-(4-hydroxy-4-methyl-piperidin-1-yl)-methanone,
[6-bromo-1-(2-chloro-pyridin-4-yl)-5-(1-isopropyl-piperidin-4-yloxy)-1H-indol-2-yl]-morpholin-4-yl-methanone,
[6-bromo-1-(2-chloro-pyridin-4-yl)-5-(1-isopropyl-piperidin-4-yloxy)-1H-indol-2-yl]-(4,4-difluoro-piperidin-1-yl)-methanone,
[5-(1-cyclobutyl-piperidin-4-yloxy)-1-pyrimidin-5-yl-1H-indol-2-yl]-(4,4-difluoro-piperidin-1-yl)-methanone,
(4-hydroxy-4-methyl-piperidin-1-yl)-[5-(1-isopropyl-piperidin-4-yloxy)-1-pyrimidin-5-yl-1H-indol-2-yl]-methanone,
[5-(1-cyclobutyl-piperidin-4-yloxy)-1-pyrimidin-5-yl-1H-indol-2-yl]-(4-hydroxy-4-methyl-piperidin-1-yl)-methanone, and pharmaceutically acceptable salts thereof.

Furthermore, the pharmaceutically acceptable salts of the compounds of formula I and the pharmaceutically acceptable esters of the compounds of formula I individually constitute preferred embodiments of the present invention.

Compounds of formula I may form acid addition salts with acids, such as conventional pharmaceutically acceptable acids, for example hydrochloride, hydrobromide, phosphate, acetate, fumarate, maleate, salicylate, sulphate, pyruvate, citrate, lactate, mandelate, tartarate and methanesulphonate. Preferred are the hydrochloride salts. Also solvates and hydrates of compounds of formula I and their salts form part of the present invention.

Compounds of formula I can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbens or eluant). The invention embraces all of these forms.

It will be appreciated, that the compounds of general formula I in this invention may be derivatized at functional groups to provide derivatives which are capable of conversion back to the parent compound in vivo. Physiologically acceptable and metabolically labile derivatives, which are capable of producing the parent compounds of general formula I in vivo are also within the scope of this invention.

A further aspect of the present invention is the process for the manufacture of compounds of formula I as defined above, which process comprises treating a compound of the formula II

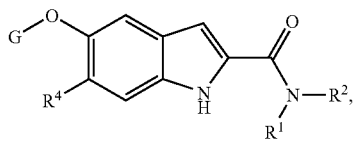

wherein $R^1$, $R^2$ and $R^4$ are as defined herein before, with a suitable base in a suitable solvent under anhydrous conditions and reacting the intermediate anion with an alkylating or acylating agent of the formula III $$R^3\text{—}X \qquad \text{III,}$$

wherein X signifies a leaving group and $R^3$ is selected from the group consisting of lower hydroxyalkyl, lower cyanoalkyl, optionally substituted lower phenylalkyl, lower alkoxycarbonyl and optionally substituted phenylsulfonyl,

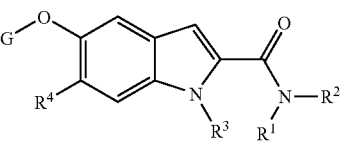

wherein $R^3$ is selected from the group consisting of lower hydroxyalkyl, lower cyanoalkyl, optionally substituted lower phenylalkyl, lower alkoxycarbonyl and optionally substituted phenylsulfonyl,
and if desired,
converting the compound obtained into a pharmaceutically acceptable acid addition salt, or alternatively,
reacting a compound of formula II

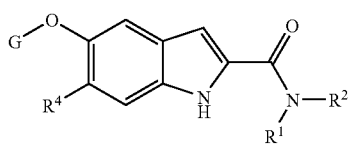

wherein $R^1$, $R^2$ and $R^4$ are as defined herein before, with an optionally substituted phenyl- or heteroaryl boronic acid of the formula IV

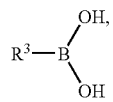

wherein $R^3$ signifies optionally substituted aryl or heteroaryl, in the presence of a catalyst and basic conditions to obtain a compound of the formula

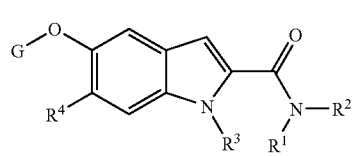

wherein $R^3$ signifies optionally substituted aryl or optionally substituted heteroaryl, and if desired,
converting the compound obtained into a pharmaceutically acceptable acid addition salt.

Treating a compound of formula II with a suitable base in a suitable solvent under anhydrous conditions means e.g. treating the compound with sodium hydride in a solvent such as dimethylformamide (DMF) to obtain the intermediate anion which is then reacted with an alkylating or acylating agent $R^3$—X, wherein X signifies a leaving group such as e.g. iodide, bromide, methanesulfonate or chloride, to obtain a compound of formula Ia wherein $R^3$ is selected from the group consisting of lower hydroxyalkyl, lower cyanoalkyl, optionally substituted lower phenylalkyl, lower alkoxycarbonyl and optionally substituted phenylsulfonyl. Compounds of formula Ib, wherein $R^3$ signifies optionally substituted aryl or optionally substituted heteroaryl, are obtained by reacting a compound of formula II with an optionally substituted phenylboronic acid using an appropriate catalyst (e.g. copper(II) acetate) and base (e.g. pyridine) in a suitable solvent like, e.g. dichloromethane.

In more detail, the compounds of formula I can be manufactured by the methods given below, by the methods given in the examples or by analogous methods. Appropriate reaction conditions for the individual reaction steps are known to a person skilled in the art. Starting materials are either commercially available or can be prepared by methods analogous to the methods given below, by methods described in references cited in the description or in the examples, or by methods known in the art.

The preparation of compounds of formula I of the present invention may be carried out in sequential or convergent synthetic routes. Syntheses of the invention are shown in the following schemes. The skills required for carrying out the reaction and purification of the resulting products are known to those skilled in the art. The substituents and indices used in the following description of the processes have the significance given herein before unless indicated to the contrary.

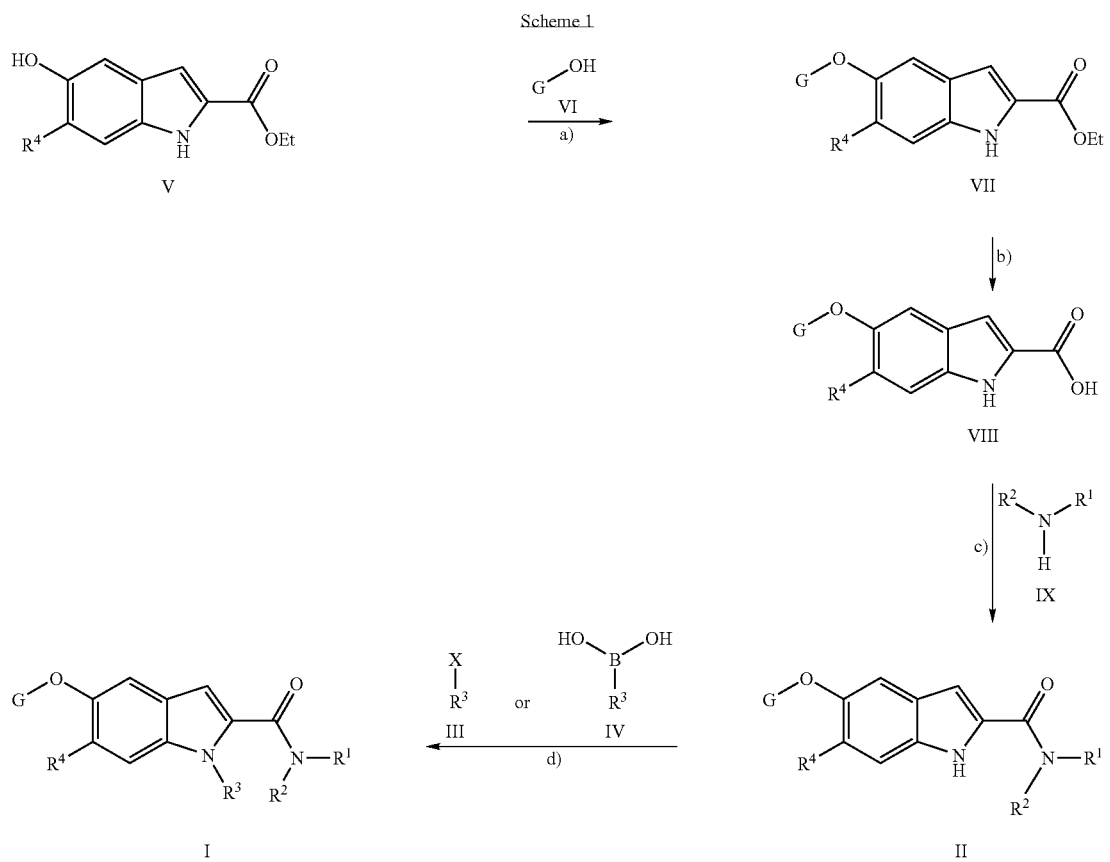

Scheme 1

Compounds of general formula I can be prepared according to scheme 1 as follows:

The methods how to synthesize ethers of formula VII are widely described in literature and the procedures are known to those in the art (For reaction conditions described in literature affecting such reactions, see for example: Comprehensive Organic Transformations: A Guide to Functional Group Preparations, 2nd Edition, Richard C. Larock. John Wiley & Sons, New York, N.Y. 1999). The transformation can be affected by employing reaction conditions which are commonly utilised in the so called "Mitsunobu reaction" which is known to those in the art and widely described (Hughes, David L. The Mitsunobu reaction. Organic Reactions, New York, 1992 42 335-656.) We find it convenient to couple hydroxyindole V with alcohols VI (either commercially available or accessible by methods described in references or by methods known in the art, as appropriate) under conditions employing a phosphine like tributylphosphine, triphenylphosphine and the like and a diazo-compound like diethyl-azodicarboxylate, diisopropyl-azodicarboxylate (optionally polymer bound), di-tert-butylazodicarboxylate, tetramethyl azodicarboxamide and the like in a solvent commonly used in such transformations like tetrahydrofuran, toluene, dichloromethane and the like. There is no particular restriction on the nature of the solvent to be employed, provided that it has no adverse effect on the reaction or the reagents involved and that it can dissolve the reagents, at least to some extent. The reaction can take place over a wide range of temperatures and the precise reaction temperature is not critical to the invention. We find it convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield the compounds of formula VII.

The compounds of formula VII are transformed into the free acids VIII under basic conditions, for example by using lithium hydroxide monohydrate as a base.

The coupling of carboxylic acids with amines is widely described in literature and the procedures are known to those in the art (For reaction conditions described in literature affecting such reactions see for example: Comprehensive Organic Transformations: A Guide to Functional Group Preparations, 2nd Edition, Richard C. Larock. John Wiley & Sons, New York, N.Y. 1999). Carboxylic acid VIII can conveniently be transformed to the respective amide II through coupling with an amine IX (either commercially available or accessible by methods described in references or by methods known in the art; as appropriate) by employing the usage of coupling reagents. For example coupling reagents like N,N'-carbonyldiimidazole, N,N'-dicyclohexylcarbo-diimide, 1-(3-dimethylaminopropyl)-3-ethylcarbodiimide hydrochloride, 1-[bis(dimethylamino)methylene]-1H-1,2,3-triazolo[4,5-b]pyridinium-3-oxide hexafluorophosphate, 1-hydroxy-1,2,3-benzotriazole, O-benzotriazol-1-yl-N,N,N',N'-tetramethyluronium tetrafluoroborate and the like can equally well be employed to affect such transformation. We find it convenient to carry out the reaction in a solvent and in the presence of a base. There is no particular restriction on the nature of the solvent to be employed, provided that it has no adverse effect on the reaction or the reagents involved and that it can dissolve the reagents, at least to some extent. Examples for suitable solvents include: N,N-dimethylformamide, dichloromethane, dioxane, tetrahydrofuran and the like. There is no particular restriction on the nature of the base used in this stage and any base commonly used in this type of reaction may equally be employed here. Examples of such bases include triethylamine and diisopropylethylamine and the like. The reaction can take place over a wide range of temperatures and the precise reaction temperature is not critical to the invention.

We find it convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield amide derivatives II.

Compounds II can be subjected to reaction in which the indole NH will be substituted by lower alkyl substituents, benzyl substituents, alkyl and arylsulfonyl substituents through a reaction with an alkylating or acylating agent III (either commercially available or accessible by methods described in references or by methods known in the art, as appropriate). Conditions commonly used in such types of transformation are widely described in literature and known to those in the art. The leaving group X can be any halogen group (chlorine, bromine, iodine) or pseudo halogen group (e.g. trifluoromethane-sulfonyl, para-toluenesulfonyl, methanesulfonyl and the like). The reaction might be carried out in the presence or absence of a solvent and preferably in the presence of a base. Solvents like N,N-dimethyl acetamide, N,N-dimethylformamide, tetrahydrofuran, diethyl ether, dioxane, acetonitrile, butanone and the like are conveniently used. There is no particular restriction on the nature of the solvent to be employed, provided that it has no adverse effect on the reaction or the reagents involved and that it can dissolve the reagents, at least to some extent. Usually the reaction is carried out in the presence of a base. Suitable bases include sodium hydride, diisopropylethylamine, sodium carbonate, cesium carbonate and the like. The reaction can take place over a wide range of temperatures and the precise reaction temperature is not critical to the invention. We find it convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield the desired compounds of formula I.

Alternatively, a compound of formula II can be arylated by a boronic acid or a boronic ester of formula IV (either commercially available or accessible by methods described in references or by methods known in the art, as appropriate). Conditions commonly used in such types of transformation are described in literature and known to those in the art (e.g. Mederski, W. W. K. R.; Lefort, M.; Germann, M. Kux, D. Tetrahedron 1999 55 12757). $R^3$ can be any aryl or heteroaryl compounds.

Alternatively, compound VII can be arylated by compound III (either commercially available or accessible by methods described in references or by methods known in the art; as appropriate). The transformation can be affected by employing reaction conditions which are known to those in the art and widely described (e.g. Watanabe, M; Nishiyama, M.; Yamamoto, T.; Koie, Y, Tetrahedron Letters 2000, 41, 481; Old, D. W.; Harris, M. C.; Buchwald, S. L 2000 2 10 1403; Klapars, A.; Antilla, J. C.; Huang, X.; Buchwald, S. L. J. Am. Chem. Soc. 2001 123 7727). The leaving group X can be any halogen group (chlorine, bromine, iodine) or pseudo halogen group (e.g. trifluoromethylmethanesulfonyl, paratoluenesulfonyl, methanesulfonyl and the like) and $R^3$ can be any aryl or heteroaryl compounds.

Compounds of formula I, wherein G signifies G4, can also prepared according to a method as described in scheme 2.

Compound X can be subjected to reaction in which the indole NH will be substituted by lower alkyl substituents, benzyl substituents, alkyl and arylsulfonyl substituent through a reaction with an acylating or alkylating agent III (either commercially available or accessible by methods described in references or by methods known in the art, as appropriate). Conditions commonly used in such types of transformation are widely described in literature and known to those in the art. The leaving group X can be any halogen group (chlorine, bromine, iodine) or pseudo halogen group (e.g. trifluoromethylmethane-sulfonyl, paratoluensulfonyl, methanesulfonyl and the like). The reaction might be carried out in the presence or absence of a solvent and preferably in the presence of a base. Solvents like N,N-dimethyl acetamide, N,N-dimethylformamide, tetrahydrofuran, diethyl ether, dioxane, acetonitrile, butanone and the like are conveniently used. There is no particular restriction on the nature of the solvent to be employed, provided that it has no adverse effect on the reaction or the reagents involved and that it can dissolve the reagents, at least to some extent. Usually the reaction is carried out in the presence of a base. Suitable bases include sodium hydride, diisopropylethylamine, sodium carbonate, cesium carbonate and the like. The reaction can take place over a wide range of temperatures and the precise reaction temperature is not critical to the invention. We find it convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield the compounds of formula XI.

Alternatively, compound X can be alkylated or arylated by a boronic acid or a boronic ester of formula IV (either commercially available or accessible by methods described in references or by methods known in the art, as appropriate). Conditions commonly used in such types of transformation are described in literature and known to those in the art (e.g. Mederski, W. W. K. R.; Lefort, M.; Germann, M. Kux, D. Tetrahedron 1999 55 12757). $R^3$ can be any aryl, cycloalkyl or heteroaryl compounds.

Alternatively, compound X can be arylated by a compound III wherein $R^3$ can be any optionally substituted aryl or heteroaryl group (either commercially available or accessible by methods described in references or by methods known in the art; as appropriate). The transformation can be affected by employing reaction conditions which are known to those in the art and widely described (e.g. Watanabe, M; Nishiyama, M.; Yamamoto, T.; Koie, Y, Tetrahedron Letters 2000, 41, 481; Old, D. W.; Harris, M. C.; Buchwald, S. L 2000 2 10 1403; Klapars, A.; Antilla, J. C.; Huang, X.; Buchwald, S. L. J. Am. Chem. Soc. 2001 123 7727). The leaving group X can be any halogen group (chlorine, bromine, iodine) or pseudo halogen group (e.g. trifluoromethylmethanesulfonyl, paratoluensulfonyl, methanesulfonyl and the like).

The compounds of formula XI are transformed into the free acids XII under basic conditions, for example by using lithium hydroxide monohydrate as a base.

The coupling of carboxylic acids with amines is widely described in literature and the procedures are known to those in the art (For reaction conditions described in literature affecting such reactions, see for example: Comprehensive Organic Transformations: A Guide to Functional Group Preparations, 2nd Edition, Richard C. Larock. John Wiley & Sons, New York, N.Y. 1999). Carboxylic acid XII can conveniently be transformed to the respective amide XIII through coupling with an amine IX (either commercially available or accessible by methods described in references or by methods known in the art, as appropriate) by employing the usage of coupling reagents. For example coupling reagents like N,N'-carbonyldiimidazole, N,N'-dicyclohexylcarbodiimide, 1-(3-dimethylaminopropyl)-3-ethylcarbodiimide hydrochloride, 1-[bis(dimethylamino)methylene]-1H-1,2,3-triazolo[4,5-b]pyridinium-3-oxide hexafluorophosphate, 1-hydroxy-1,2,3-benzotriazole, O-benzotriazol-1-yl-N,N,N',N'-tetramethyluronium tetrafluoroborate and the like can equally well be employed to affect such transformation. We find it convenient to carry out the reaction in a solvent like N,N-dimethylformamide and in the presence of a base. There is no particular restriction on the nature of the solvent to be employed, provided that it has no adverse effect on the reaction or the reagents involved and that it can dissolve the reagents, at least to some extent. Examples for suitable solvents include: dimethylformamide, dichloromethane, dioxane, tetrahydrofuran and the like. There is no particular restriction on the nature of the base used in this stage and any base commonly used in this type of reaction may equally be employed here. Examples of such bases include triethylamine and diisopropylethylamine and the like. The reaction can take place over a wide range of temperatures and the precise reaction temperature is not critical to the invention.

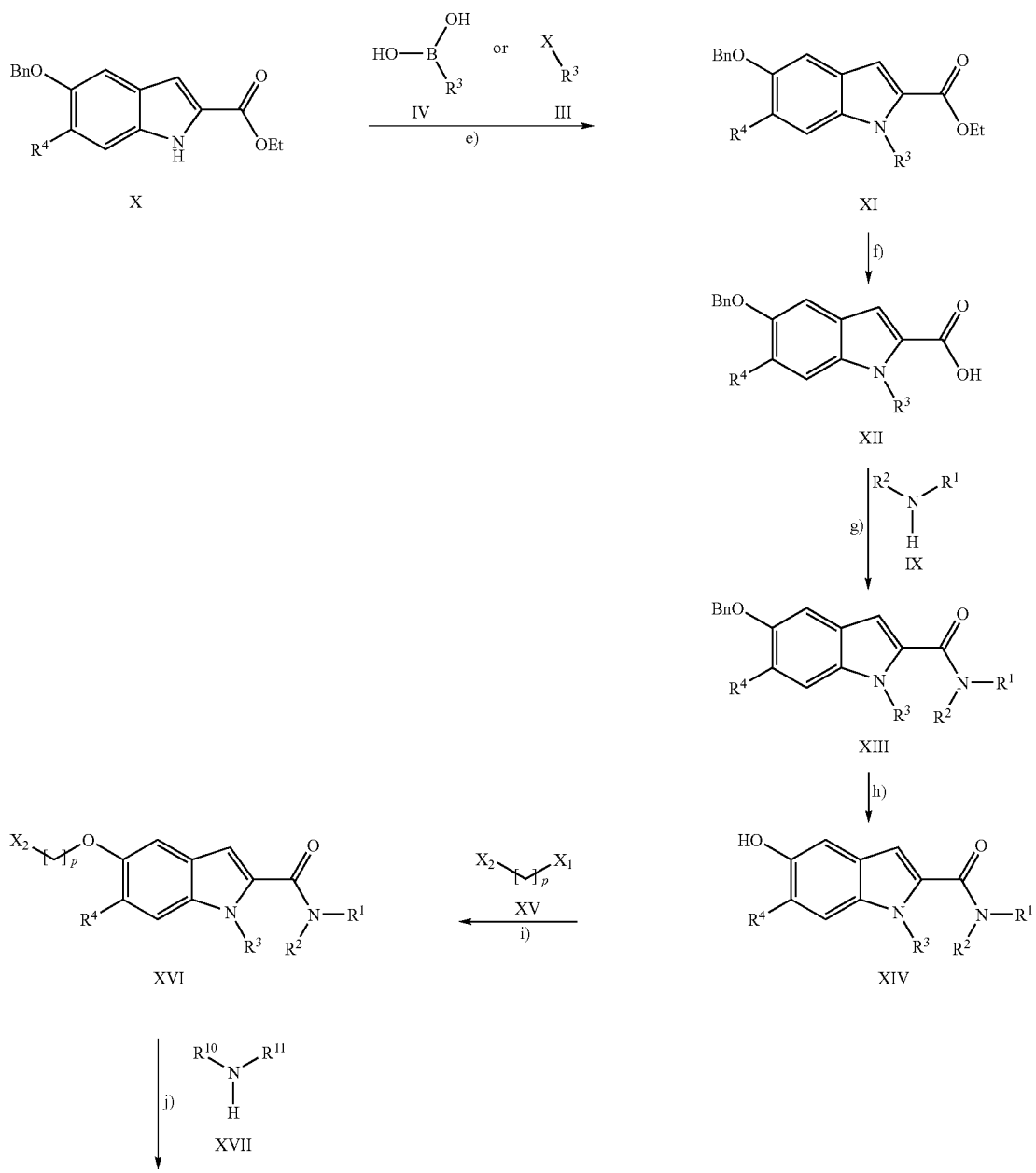

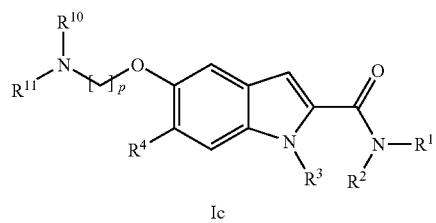

Ic

We find it convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield amide derivatives XIII.

Removal of the benzyl protective groups is performed using conditions commonly used in such types of transformation and is widely described in literature and known to those in the art (For reaction conditions described in literature affecting such reactions see for example: Protective groups in organic synthesis, 3rd Edition, Theodora W. Greene, Peter G. M. Wuts, Wiley Interscience 1999). We find it convenient to use palladium adsorbed on activated charcoal as catalyst in suitable solvent e.g. ethyl acetate, tetrahydrofuran, methanol and the like, alone or in mixture. Hydrogen gas is present under a partial pressure from 1 atm to 100 atm, yielding to compound of formula XIV.

The ether of formula XVI are prepared from 5-hydroxyindole XIV and a suitable bis halogeno (chlorine, bromine, iodine) or pseudohalogenoalkane (e.g. trifluoromethylmethanesulfonyl, paratoluensulfonyl, methanesulfonyl and the like) XV under the conditions as described under point e)

The desired compounds Ib are prepared under the conditions as described under point e) using cyclic or acyclic secondary amines XVII (either commercially available or accessible by methods described in references or by methods known in the art, as appropriate).

As described above, the compounds of formula I of the present invention can be used as medicaments for the treatment and/or prevention of diseases which are associated with the modulation of H3 receptors.

In this context, the expression 'diseases associated with the modulation of H3 receptors' means diseases which can be treated and/or prevented by modulation of H3 receptors. Such diseases encompass, but are not limited to, obesity, metabolic syndrome (syndrome X), neurological diseases including Alzheimer's disease, dementia, age-related memory dysfunction, mild cognitive impairment, cognitive deficit, attention deficit hyperactivity disorder, epilepsy, neuropathic pain, inflammatory pain, migraine, Parkinson's disease, multiple sclerosis, stroke, dizziness, schizophrenia, depression, addiction, motion sickness and sleep disorders including narcolepsy and other diseases including asthma, allergy, allergy-induced airway responses, congestion, chronic obstructive pulmonary disease and gastro-intestinal disorders.

In a preferable aspect, the expression 'diseases associated with modulation of H3 receptors' relates to obesity, metabolic syndrome (syndrome X) and other eating disorders, with obesity being especially preferred.

The invention therefore also relates to pharmaceutical compositions comprising a compound as defined above and a pharmaceutically acceptable carrier and/or adjuvant.

Further, the invention relates to compounds as defined above for use as therapeutically active substances, particularly as therapeutic active substances for the treatment and/or prevention of diseases which are associated with the modulation of H3 receptors.

In another embodiment, the invention relates to a method for the treatment and/or prevention of diseases which are associated with the modulation of H3 receptors, which method comprises administering a therapeutically active amount of a compound of formula I to a human being or animal. A method for the treatment and/or prevention of obesity is preferred.

The invention further relates to the use of compounds of formula I as defined above for the treatment and/or prevention of diseases which are associated with the modulation of H3 receptors.

In addition, the invention relates to the use of compounds of formula I as defined above for the preparation of medicaments for the treatment and/or prevention of diseases which are associated with the modulation of H3 receptors. The use of compounds of formula I as defined above for the preparation of medicaments for the treatment and/or prevention of obesity is preferred.

Furthermore, the present invention relates to the use of a compound of formula I for the manufacture of a medicament for the treatment and prevention of obesity in a patient who is also receiving treatment with a lipase inhibitor and particularly, wherein the lipase inhibitor is orlistat.

It is a further preferred embodiment of the present invention to provide a method for the treatment or prevention of obesity and obesity related disorders which comprises administration of a therapeutically effective amount of a compound according to formula I in combination or association with a therapeutically effective amount of other drugs for the treatment of obesity or eating disorders so that together they give effective relief. Suitable other drugs include, but are not limited to, anorectic agents, lipase inhibitors, selective serotonin reuptake inhibitors (SSRI) and agents that stimulate metabolism of body fat. Combinations or associations of the above agents may be encompassing separate, sequential or simultaneous administration.

The term "lipase inhibitor" refers to compounds which are capable of inhibiting the action of lipases, for example gastric and pancreatic lipases. For example orlistat and lipstatin as described in U.S. Pat. No. 4,598,089 are potent inhibitor of lipases. Lipstatin is a natural product of microbial origin and orlistat is the result of a hydrogenation of lipstatin. Other lipase inhibitors include a class of compound commonly referred to as panclicins. Panclicins are analogues of orlistat (Mutoh et al, 1994). The term "lipase inhibitor" refers also to polymer bound lipase inhibitors for example described in International Patent Application WO 99/34786 (Geltex Pharmaceuticals Inc.). These polymers are characterized in that they have been substituted with one or more groups that inhibit lipases. The term "lipase inhibitor" also comprises pharmaceutically acceptable salts of these compounds. The term "lipase inhibitor" preferably refers to tetrahydrolipstatin. Administration of a therapeutically effective amount of a compound according to formula I in combination or association with a therapeutically effective amount of tetrahydrolipstatin is especially preferred.

Tetrahydrolipstatin (orlistat) is a known compound useful for the control or prevention of obesity and hyperlipidemia. See, U.S. Pat. No. 4,598,089, issued Jul. 1, 1986, which also discloses processes for making orlistat and U.S. Pat. No. 6,004,996, which discloses appropriate pharmaceutical compositions. Further suitable pharmaceutical compositions are described for example in International Patent Applications WO 00/09122 and WO 00/09123. Additional processes for the preparation of orlistat are disclosed in European Patent Applications Publication Nos. 0 185 359, 0 189 577, 0 443 449 and 0 524 495.

Suitable anorectic agents of use in combination with a compound of the present invention include, but are not limited to, APD356, aminorex, amphechloral, amphetamine, axokine, benzphetamine, bupropion, chlorphentermine, clobenzorex, cloforex, clominorex, clortermine, CP945598, cyclexedrine, CYT009-GhrQb, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, metreleptin, norpseudoephedrine, pentorex, phendimetrazine, phenmetrazine, phentermine, phenylpropanolamine, picilorex, rimonabant, sibutramine, SLV319, SNAP 7941, SR147778 (Surinabant), steroidal plant extract (e.g. P57) and TM30338 and pharmaceutically acceptable salts thereof.

Most preferable anorectic agents are sibutramine, rimonabant and phentermine.

Suitable selective serotonin reuptake inhibitors of use in combination with a compound of the present invention include: fluoxetine, fluvoxamine, paroxetine and sertraline and pharmaceutically acceptable salts thereof.

Suitable agents that stimulate metabolism of body fat include, but are not limited to, growth hormone agonist (e.g. AOD-9604).

The use of a compound of formula I in the manufacture of a medicament for the treatment and prevention of obesity in a patient who is also receiving treatment with a compound selected from the group consisting of a lipase inhibitor, an anorectic agent, a selective serotonin reuptake inhibitor and an agent that stimulates metabolism of body fat, is also an embodiment of the present invention.

The use of a compound of formula I in the manufacture of a medicament for the treatment and prevention of obesity in a patient who is also receiving treatment with a lipase inhibitor, preferably with tetrahydrolipstatin, is also an embodiment of the present invention.

It is a further preferred embodiment to provide a method of treatment or prevention of Type II diabetes (non-insulin dependent diabetes mellitus (NIDDM)) in a human, which comprises administration of a therapeutically effective amount of a compound according to formula I in combination or association with a therapeutically effective amount of a lipase inhibitor, particularly, wherein the lipase inhibitor is tetrahydrolipstatin. Also an embodiment of the invention is the method as described above for the simultaneous, separate or sequential administration of a compound according to formula I and a lipase inhibitor, particularly tetrahydrolipstatin.

It is a further preferred embodiment to provide a method of treatment or prevention of Type II diabetes (non-insulin dependent diabetes mellitus (NIDDM)) in a human which comprises administration of a therapeutically effective amount of a compound according to formula I in combination or association with a therapeutically effective amount of an anti-diabetic agent.

The term "anti-diabetic agent" refers to compounds selected from the group consisting of 1) PPARγ agonists such as pioglitazone (actos) or rosiglitazone (avandia) and the like; 2) biguanides such as metformin (glucophage) and the like; 3) sulfonylureas such as glibenclamide, glimepiride (amaryl), glipizide (glucotrol), glyburide (DiaBeta) and the like; 4) nonsulfonylureas such as nateglinide (starlix), repaglimide (prandin) and the like; 5) PPARα/γ agonists such as GW-2331 and the like 6) DPP-IV-inhibitors such as LAF-237 (vildagliptin), MK-0431, BMS-477118 (saxagliptin) or GSK23A and the like; 7) Glucokinase activators such as the compounds disclosed in e.g. WO 00/58293 A1 and the like; 8) α-Glucosidase inhibitors such as acarbose (precose) or miglitol (glyset) and the like.

Also an embodiment of the invention is the method as described above for the simultaneous, separate or sequential administration of a compound according to formula I and a therapeutically effective amount of an anti-diabetic agent.

The use of a compound of formula I in the manufacture of a medicament for the treatment and prevention of Type II diabetes in a patient who is also receiving treatment with an anti-diabetic agent is also an embodiment of the present invention.

It is a further preferred embodiment to provide a method of treatment or prevention of dyslipidemia in a human, which comprises administration of a therapeutically effective amount of a compound according to formula I in combination or association with a therapeutically effective amount of a lipid lowering agent.

The term "lipid lowering agent" refers to compounds selected from the group consisting of 1) bile acid sequestrants such as cholestyramine (questran), colestipol (colestid) and the like; 2) HMG-CoA reductase inhibitors such as atorvastatin (lipitor), cerivastatin (baycol), fluvastatin (lescol), pravastatin (pravachol), simvastatin (zocor) and the like; 3) cholesterol absorption inhibitors such as ezetimibe and the like; 4) CETP inhibitors such as torcetrapib, JTT 705 and the like; 5) PPARα-agonists such as beclofibrate, gemfibrozil (lopid), fenofibrate (lipidil), bezafibrate (bezalip) and the like; 6) lipoprotein synthesis inhibitors such as niacin and the like; and 7) niacin receptor agonists such as nicotinic acid and the like.

Also an embodiment of the invention is the method as described above for the simultaneous, separate or sequential administration of a compound according to formula I and a therapeutically effective amount of a lipid lowering agent.

The use of a compound of formula I in the manufacture of a medicament for the treatment and prevention of dyslipidemias in a patient who is also receiving treatment with a lipid lowering agent, is also an embodiment of the present invention.

It is a further preferred embodiment to provide a method of treatment or prevention of hypertension in a human which comprises administration of a therapeutically effective amount of a compound according to formula I in combination or association with a therapeutically effective amount of an anti-hypertensive agent.

The term "anti-hypertensive agent" or "blood-pressure lowering agent" refers to compounds selected from the group consisting of 1) Angiotensin-converting Enzyme (ACE) Inhibitors including benazepril (lotensin), captopril (capoten), enalapril (vasotec), fosinopril (monopril), lisinopril (prinivil, zestril), moexipril (univasc), perindopril (coversum), quinapril (accupril), ramipril (altace), trandolapril (mavik) and the like; 2) Angiotensin II Receptor Antagonists including candesartan (atacand), eprosartan (teveten), irbesartan (avapro), losartan (cozaar), telmisartan (micadisc), valsartan (diovan) and the like; 3) Adrenergic Blockers (peripheral or central) such as the beta-adrenergic blockers including acebutolol (sectrol), atenolol (tenormin), betaxolol (kerlone), bisoprolol (zebeta), carteolol (cartrol), metoprolol (lopressor; toprol-XL), nadolol (corgard), penbutolol (levatol), pindolol (visken), propranolol (inderal), timolol (blockadren) and the like; alpha/beta adrenergic blockers including carvedilol (coreg), labetalol (normodyne) and the like; alpha-I adrenergic blockers including prazosin (minipress), doxazosin (cardura), terazosin (hytrin), phenoxybenzamine (dibenzyline) and the like; peripheral adrenergic-neuronal blockers including guanadrel (hylorel), guanethidine (ismelin), reserpine (serpasil) and the like; alpha-2 adrenergic blockers including a-methyldopa (aldomet), clonidine (catapres), guanabenz (wytensin), guanfacine (tenex) and the like; 4) Blood Vessel Dilators (Vasodilators) including hydralazine (apresoline), minoxidil (lonitren), clonidine (catapres) and the like; 5) Calcium Channel Blockers including amlodipine (norvasc), felodipine (plendil), isradipine (dynacirc), nicardipine (cardine sr), nifedipine (procardia, adalat), nisoldipine (sular), diltiazem (cardizem), verapamil (isoptil) and the like; 6) Diuretics such as thiazides and thiazides-like agents, including hydrochlorothiazide (hydrodiuril, microzide), chlorothiazide (diuril), chlorthalidone (hygroton), indapamide (lozol), metolazone (mykrox) and the like; loop diuretics, such as bumetanide (bumex) and furosemide (lasix), ethacrynic acid (edecrin), torsemide (demadex) and the like; potassium-sparing diuretics including amiloride (midamor), triamterene (dyrenium), spironolactone (aldactone) and the tiamenidine (symcor) and the like; 7) Tyrosine Hydroxylase Inhibitors, including metyrosine (demser) and the like; 8) Neutral Endopeptidase Inhibitors, including BMS-186716 (omapatrilat), UK-79300 (candoxatril), ecadotril (sinorphan), BP-1137 (fasidotril), UK-79300 (sampatrilat) and the like; and 9) Endothelin Antagonists including tezosentan (RO0610612), A308165 and the like.

Also an embodiment of the invention is the method as described above for the simultaneous, separate or sequential administration of a compound according to formula I and a therapeutically effective amount of a anti-hypertensive agent.

The use of a compound of formula I in the manufacture of a medicament for the treatment and prevention of hypertension in a patient who is also receiving treatment with an anti-hypertensive agent, is also an embodiment of the present invention.

As described above, the compounds of formula I and their pharmaceutically acceptable salts possess valuable pharmacological properties. Specifically, it has been found that the compounds of the present invention are good histamine 3 receptor (H3R) antagonists and/or inverse agonists.

The following test was carried out in order to determine the activity of the compounds of formula (I).

Binding Assay with $^3$H-(R)α-methylhistamine

Saturation binding experiments were performed using HR3-CHO membranes prepared as described in Takahashi, K, Tokita, S., Kotani, H. (2003) J. Pharmacol. Exp. Therapeutics 307, 213-218.

An appropriate amount of membrane (60 to 80 μg protein/well) was incubated with increasing concentrations of $^3$H(R) α-Methylhistamine di-hydrochloride (0.10 to 10 nM). Non specific binding was determined using a 200 fold excess of cold (R)α-Methylhistamine dihydrobromide (500 nM final concentration). The incubation was carried out at room temperature (in deep-well plates shaking for three hours). The final volume in each well was 250 μl. The incubation was followed by rapid filtration on GF/B filters (pre-soaked with 100 μl of 0.5% PEI in Tris 50 mM shaking at 200 rpm for two hours). The filtration was made using a cell-harvester and the filter plates were then washed five times with ice cold washing buffer containing 0.5 M NaCl. After harvesting, the plates were dried at 55° C. for 60 min, then scintillation fluid (Microscint 40, 40 microl in each well) was added and the amount of radioactivity on the filter was determined with a Packard top-counter after shaking the plates for two hours at 200 rpm at room temperature.

Binding Buffer: 50 mM Tris-HCl pH 7.4 and 5 mM $MgCl_2$x$6H_2O$ pH 7.4. Washing Buffer: 50 mM Tris-HCl pH 7.4 and 5 mM $MgCl_2$x$6H_2O$ and 0.5 M NaCl pH 7.4.

Indirect measurement of affinity of H3R inverse agonists: twelve increasing concentrations (ranging from 10 μM to 0.3 nM) of the selected compounds were always tested in competition binding experiments using membrane of the human HR3-CHO cell line. An appropriate amount of protein, e.g. approximately 500 cpm binding of RAMH at Kd, were incubated for 1 hour at room temperature in 250 μl final volume in 96-well plates in presence of $^3$H(R)α-Methylhistamine (1 nM final concentration=Kd). Non-specific binding was determined using a 200 fold excess of cold (R)α-Methylhistamine dihydrobromide.

All compounds were tested at a single concentration in duplicates. Compounds that showed an inhibition of [$^3$H]-RAMH by more than 50% were tested again to determine $IC_{50}$ in a serial dilution experiment. Ki's were calculated from $IC_{50}$ based on Cheng-Prusoff equation (Cheng, Y, Prusoff, W H (1973) Biochem Pharmacol 22, 3099-3108).

The compounds of the present invention exhibit $K_i$ values within the range of about 0.1 nM to about 1000 nM, preferably of about 0.1 nM to about 100 nM and more preferably of about 0.1 nM to about 30 nM. The following table shows measured values for some selected compounds of the present invention.

|  | $K_i$ (nM) |
| --- | --- |
| Example 5 | 3 |
| Example 9 | 2 |

Demonstration of additional biological activities of the compounds of the present invention may be accomplished through in vitro, ex vivo and in vivo assays that are well known in the art. For example, to demonstrate the efficacy of a pharmaceutical agent for the treatment of obesity-related disorders such as diabetes, Syndrome X, or atherosclerotic disease and related disorders such as hypertriglyceridemia and hypercholesteremia, the following assays may be used.

Method for Measuring Blood Glucose Levels db/db mice (obtained from Jackson Laboratories, Bar Harbor, Me.) are bled (by either eye or tail vein) and grouped according to equivalent mean blood glucose levels. They are dosed orally (by gavage in a pharmaceutically acceptable vehicle) with the test compound once daily for 7 to 14 days. At this point, the animals are bled again by eye or tail vein and blood glucose levels are determined.

Method for Measuring Triglyceride Levels hApoAl mice (obtained from Jackson Laboratories, Bar Harbor, Me.) are bled (by either eye or tail vein) and grouped according to equivalent mean serum triglyceride levels. They are dosed orally (by gavage in a pharmaceutically acceptable vehicle) with the test compound once daily for 7 to 14 days. The animals are then bled again by eye or tail vein and serum triglyceride levels are determined.

Method for Measuring HDL-Cholesterol Levels

To determine plasma HDL-cholesterol levels, hApoAl mice are bled and grouped with equivalent mean plasma HDL-cholesterol levels. The mice are orally dosed once daily with vehicle or test compound for 7 to 14 days and then bled on the following day. Plasma is analyzed for HDL-cholesterol.

The compounds of formula (I) and their pharmaceutically acceptable salts and esters can be used as medicaments, e.g. in the form of pharmaceutical preparations for enteral, parenteral or topical administration. They can be administered, for example, perorally, e.g. in the form of tablets, coated tablets, dragees, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils.

The production of the pharmaceutical preparations can be effected in a manner which will be familiar to any person skilled in the art by bringing the described compounds of formula (I) and their pharmaceutically acceptable salts and esters, into a galenical administration form together with suitable, non-toxic, inert, therapeutically compatible solid or liquid carrier materials and if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragees and hard gelatine capsules. Suitable carrier materials for soft gelatine capsules are, for example, vegetable oils, waxes, fats and semi-solid and liquid polyols (depending on the nature of the active ingredient no carriers are, however, required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavor-improving agents, salts for varying the osmotic pressure, buffer substances, solubilizers, colorants and masking agents and antioxidants come into consideration as pharmaceutical adjuvants.

The dosage of the compounds of formula (I) can vary within wide limits depending on the disease to be controlled, the age and the individual condition of the patient and the mode of administration and will, of course, be fitted to the individual requirements in each particular case. For adult patients a daily dosage of about 1 mg to about 1000 mg, especially about 1 mg to about 100 mg, comes into consideration. Depending on the dosage it is convenient to administer the daily dosage in several dosage units.

The pharmaceutical preparations conveniently contain about 0.1-500 mg, preferably 0.5-100 mg, of a compound of formula (I).

The following examples serve to illustrate the present invention in more detail. They are, however, not intended to limit its scope in any manner.

EXAMPLES

Intermediates

Intermediate 1

(4,4-Difluoro-piperidin-1-yl)-[5-(1-isopropyl-piperidin-4-yloxy)-1H-indol-2-yl]-methanone Step 1: 1-Isopropyl-piperidin-4-ol To a cold solution of 1-isopropylpiperidone (purchased at Chemie Brunschwig AG, 100 g, 1.0 eq.) in ethanol (500 mL) was added sodium borohydride (19.3 g, 0.7 eq.) in small portions. The reaction mixture was allowed to warm up to room temperature and was stirred overnight. After concentrating the mixture in vacuo, ice water (1 kg), sodium hydroxide aqueous solution (28% in mass, 0.5 L) and dichloromethane (1 L) were added. The mixture was stirred vigorously for 4 h and the aqueous layer was extracted with dichloromethane. Combined organic layers were washed with brine, dried over sodium sulfate, filtered and purified by fractionated vacuum distillation (20 mbar). One fraction (boiling point 95° C. at 20 mBar) was isolated to yield 61.3 g (60%) of the desired product as colorless oil. MS (m/e): 144.5 (MH$^+$, 100%).

Step 2: 5-(1-Isopropyl-piperidin-4-yloxy)-1H-indole-2-carboxylic acid ethyl ester To a cold (0° C.) solution of 5-hydroxyindole-2-carboxylic acid ethyl ester (purchased at Biosynth, ref H-6350, 20 g, 1.0 eq.), 1-isopropylpiperidin-4-ol (intermediate 1, step 1, 16.75 g, 1.2 eq.) and triphenylphosphine (30.68 g, 1.2 eq.) in tetrahydrofuran (500 mL) was slowly added a solution of di-tert-butylazodicarboxylate (26.93 g, 1.2 eq.) in tetrahydrofuran (100 mL). The reaction mixture was stirred at room temperature for 48 h then evaporated to dryness in vacuo and purified on silica, eluting with a gradient of solvent from dichloromethane/ethyl acetate 19:1 to dichloromethane/methanol/ammonium hydroxide 95:5:0.25. One fraction was isolated and dried in vacuo, to yield 21.53 g (66%) of the desired product as white solid. MS (m/e): 331.1 (MH$^+$, 100%).

Step 3: 5-(1-Isopropyl-piperidin-4-yloxy)-1H-indole-2-carboxylic acid hydrochloride salt with 1 equivalent of lithium chloride A mixture of 5-(1-isopropyl-piperidin-4-yloxy)-1H-indole-2-carboxylic acid ethyl ester (intermediate 1, step 2, 21 g, 1.0 eq.), lithium hydroxide monohydrate (3.23 g, 1.21 eq.), water (80 mL), methanol (50 mL) and tetrahydrofuran (150 mL) was heated under reflux for 4 h, then concentrated to a volume of 50 mL. The pH was adjusted to 1-2 using a solution of hydrochloric acid (2N). The volatiles were removed in vacuo and the crude solid was dissolved in ethanol/methanol 1:1. The solid was filtered off and the mother liquor was concentrated in vacuo. Tert-butyl methyl ether (100 mL) were added and the resulting solid was filtered and dried in vacuo to yield 16.69 g (69%) of the desired product as white solid. MS (m/e): 303.0 (MH$^+$, 100%).

Step 4: (4,4-Difluoro-piperidin-1-yl)-[5-(1-isopropyl-piperidin-4-yloxy)-1H-indol-2-yl]-methanone A mixture of 5-(1-isopropyl-piperidin-4-yloxy)-1H-indole-2-carboxylic acid hydrochloride salt with 1 equivalent of lithium chloride (Intermediate 1, step 3, 5.0 g, 1.0 eq.), 2-(1H-benzotriazole-1-yl)-1,1,3,3-tetramethyluronium tetrafluoroborate (5.26 g, 1.2 eq.), 4,4'-difluoropiperidine hydrochloride (2.48 g, 1.2 eq.) and N-ethyldiisopropylamine (11.46 mL, 5 eq.) in N,N-dimethylformamide (75 mL) was stirred at room temperature for 17 h. The reaction mixture was diluted with ethyl acetate and washed with saturated sodium bicarbonate solution, water and brine, then dried over sodium sulfate, filtered and concentrated in vacuo. Tert-butyl methyl ether (40 mL) were added. The precipitate was filtered, washed with tert-butyl methyl ether and dried in vacuo to yield 4.96 g (93%) of the desired product as white solid. MS (m/e): 406.3 (MH$^+$, 100%).

Intermediate 2

[5-(1-Isopropyl-piperidin-4-yloxy)-1H-indol-2-yl]-morpholin-4-yl-methanone

In analogy to the procedure described for the synthesis of intermediate 1, the title compound was synthesized from 5-(1-isopropyl-piperidin-4-yloxy)-1H-indole-2-carboxylic acid difluoropiperidine hydrochloride salt with one equivalent of lithium chloride (intermediate 1, step 3) and morpholine. The title compound was obtained in 60% yield as off-white solid. MS (m/e): 372.5 (MH$^+$, 100%).

Example 1

(4,4-Difluoro-piperidin-1-yl)-[1-(4-fluoro-benzenesulfonyl)-5-(1-isopropyl-piperidin-4-yloxy)-1H-indol-2-yl]-methanone Sodium hydride (60% dispersion in oil, 24 mg, 1.1 eq.) was added to a mixture of (4,4-difluoro-piperidin-1-yl)-[5-(1-isopropyl-piperidin-4-yloxy)-1H-indol-2-yl]-methanone (intermediate 1, 200 mg, 1.0 eq.) in N,N-dimethylformamide (2 mL) and stirred at 70° C. for 30 min. 4-Fluorobenzenesulfonyl chloride (115 mg, 1.2 eq.) was added and the reaction mixture was stirred at 70° C. overnight. The reaction mixture was partitioned between ethyl acetate and water. The aqueous layer was extracted with ethyl acetate and the combined organic fractions were washed with water and brine, dried over sodium sulfate, filtered, evaporated to dryness and purified on silica gel, eluting with dichloromethane/methanol 49:1 to yield 167 mg (60%) of the desired product as yellow foam. MS (m/e): 564.4 (MH$^+$, 100%).

Example 2

[1-Benzyl-5-(1-isopropyl-piperidin-4-yloxy)-1H-indol-2-yl]-morpholin-4-yl-methanone In analogy to the procedure described for the synthesis of example 1, the title compound was synthesized from [5-(1-isopropyl-piperidin-4-yloxy)-1H-indol-2-yl]-morpholin-4-yl-methanone (intermediate 2) and benzyl bromide. The title compound was obtained in 4% yield as white solid. MS (m/e): 462.2 (MH$^+$, 100%).

Example 3

(4,4-Difluoro-piperidin-1-yl)-[1-(4-fluoro-benzyl)-5-(1-isopropyl-piperidin-4-yloxy)-1H-indol-2-yl]-methanone In analogy to the procedure described for the synthesis of example 1, the title compound was synthesized from (4,4-difluoro-piperidin-1-yl)-[5-(1-isopropyl-piperidin-4-yloxy)-1H-indol-2-yl]-methanone (intermediate 1) and 4-fluorobenzyl bromide. The title compound was obtained in 5% yield as yellow oil. MS (m/e): 514.3 (MH$^+$, 100%).

Example 4

2-(4,4-Difluoro-piperidine-1-carbonyl)-5-(1-isopropyl-piperidin-4-yloxy)-indole-1-carboxylic acid methyl ester A solution of (4,4-difluoro-piperidin-1-yl)-[5-(1-isopropyl-piperidin-4-yloxy)-1H-indol-2-yl]-methanone (intermediate 1, 100 mg, 1.0 eq.), lithium bis-(trimethylsilyl)amide (1M solution in tetrahydrofuran, 271 ul, 1.1 eq.) and methylchloroformate (26 mg, 1.1 eq.) in tetrahydrofuran (2 mL) was stirred at room temperature for 48 h, then poured into brine, extracted with dichloromethane, dried over sodium sulfate, filtered, evaporated to dryness and purified on silica gel, eluting with a 98:2 to 97:3 gradient of dichloromethane/methanol, to yield 18 mg (15%) of the desired product as yellow oil. MS (m/e): 464.2 (MH$^+$, 100%).

Example 5

[2-(4,4-Difluoro-piperidine-1-carbonyl)-5-(1-isopropyl-piperidin-4-yloxy)-indol-1-yl]-acetonitrile In analogy to the procedure described for the synthesis of Example 1, the title compound was synthesized from (4,4-difluoro-piperidin-1-yl)-[5-(1-isopropyl-piperidin-4-yloxy)-1H-indol-2-yl]-methanone (intermediate 1) and bromoacetonitrile. The title compound was obtained in 38% yield as light green foam. MS (m/e): 445.2 (MH$^+$, 100%).

Example 6

[1-(3,5-Difluoro-phenyl)-5-(1-isopropyl-piperidin-4-yloxy)-1H-indol-2-yl]-(4,4-difluoro-piperidin-1-yl)-methanone A mixture of (4,4-difluoro-piperidin-1-yl)-[5-(1-isopropyl-piperidin-4-yloxy)-1H-indol-2-yl]-methanone (intermediate 1, 100 mg, 1.0 eq.), anhydrous copper(II) acetate (90 mg, 2.0 eq.), 3,5-difluorophenylboronic acid (123 mg, 3 eq.) and pyridine (80 uL, 4 eq.) in dichloromethane (2.5 mL) was stirred at room temperature for 2 days, evaporated to dryness and purified on silica gel, eluting with a 98:2 to 95:5 gradient of dichloromethane/methanol, to yield 79 mg (61%) from the desired product as light yellow foam. MS (m/e): 518.4 (MH$^+$, 100%).

Example 7

(4,4-Difluoro-piperidin-1-yl)-[5-(1-isopropyl-piperidin-4-yloxy)-1-(3-trifluoromethoxy-phenyl)-1H-indol-2-yl]-methanone In analogy to the procedure described for the synthesis of example 6, the title compound was synthesized from (4,4-difluoro-piperidin-1-yl)-[5-(1-isopropyl-piperidin-4-yloxy)-1H-indol-2-yl]-methanone (intermediate 1) and 3-trifluoromethoxybenzene boronic acid. The title compound was obtained in 73% yield as light green foam. MS (m/e): 566.4 (MH+, 100%).

Example 8

(4,4-Difluoro-piperidin-1-yl)-[5-(1-isopropyl-piperidin-4-yloxy)-1-(4-trifluoromethoxy-phenyl)-1H-indol-2-yl]-methanone In analogy to the procedure described for the synthesis of example 6, the title compound was synthesized from (4,4-difluoro-piperidin-1-yl)-[5-(1-isopropyl-piperidin-4-yloxy)-1H-indol-2-yl]-methanone (intermediate 1) and 4-trifluoromethoxybenzene boronic acid. The title compound was obtained in 84% yield as white foam. MS (m/e): 566.4 (MH+, 100%).

Example 9

[1-(2-Chloro-pyridin-4-yl)-5-(1-isopropyl-piperidin-4-yloxy)-1H-indol-2-yl]-(4,4-difluoro-piperidin-1-yl)-methanone In analogy to the procedure described for the synthesis of example 6, the title compound was synthesized from (4,4-difluoro-piperidin-1-yl)-[5-(1-isopropyl-piperidin-4-yloxy)-1H-indol-2-yl]-methanone (intermediate 1) and 2-chloropyridine-4-boronic acid. The title compound was obtained in 10% yield as light yellow foam. MS (m/e): 517.2 (MH+, 100%).

Example 10

[1-(6-Chloro-pyridin-3-yl)-5-(1-isopropyl-piperidin-4-yloxy)-1H-indol-2-yl]-(4,4-difluoro-piperidin-1-yl)-methanone In analogy to the procedure described for the synthesis of example 6, the title compound was synthesized from (4,4-difluoro-piperidin-1-yl)-[5-(1-isopropyl-piperidin-4-yloxy)-1H-indol-2-yl]-methanone (intermediate 1) and 2-chloropyridine-5-boronic acid. The title compound was obtained in 36% yield as orange foam. MS (m/e): 517.3 (MH+, 100%).

Example 11

(4,4-Difluoro-piperidin-1-yl)-[5-(1-isopropyl-piperidin-4-yloxy)-1-(2-methoxy-phenyl)-1H-indol-2-yl]-methanone In analogy to the procedure described for the synthesis of example 6, the title compound was synthesized from (4,4-difluoro-piperidin-1-yl)-[5-(1-isopropyl-piperidin-4-yloxy)-1H-indol-2-yl]-methanone (intermediate 1) and 2-methoxyphenylboronic acid. The title compound was obtained in 7% yield as yellow oil. MS (m/e): 512.3 (MH+, 100%).

Example 12

(4,4-Difluoro-piperidin-1-yl)-[1-(4-fluoro-phenyl)-5-(1-isopropyl-piperidin-4-yloxy)-1H-indol-2-yl]-methanone In analogy to the procedure described for the synthesis of example 6, the title compound was synthesized from (4,4-difluoro-piperidin-1-yl)-[5-(1-isopropyl-piperidin-4-yloxy)-1H-indol-2-yl]-methanone (intermediate 1) and 4-fluorobenzeneboronic acid. The title compound was obtained in 93% yield as yellow foam. MS (m/e): 500.2 (MH+, 100%).

Example 13

(4,4-Difluoro-piperidin-1-yl)-[1-(3-fluoro-phenyl)-5-(1-isopropyl-piperidin-4-yloxy)-1H-indol-2-yl]-methanone In analogy to the procedure described for the synthesis of example 6, the title compound was synthesized from (4,4-difluoro-piperidin-1-yl)-[5-(1-isopropyl-piperidin-4-yloxy)-1H-indol-2-yl]-methanone (intermediate 1) and 3-fluorobenzeneboronic acid. The title compound was obtained in 97% yield as yellow foam. MS (m/e): 500.1 (MH+, 100%).

Example 14

[1-(3-Chloro-phenyl)-5-(1-isopropyl-piperidin-4-yloxy)-1H-indol-2-yl]-(4,4-difluoro-piperidin-1-yl)-methanone In analogy to the procedure described for the synthesis of example 6, the title compound was synthesized from (4,4-difluoro-piperidin-1-yl)-[5-(1-isopropyl-piperidin-4-yloxy)-1H-indol-2-yl]-methanone (intermediate 1) and 3-chlorophenylboronic acid. The title compound was obtained in 71% yield as yellow foam. MS (m/e): 516.2 (MH+, 100%).

Example 15

(4,4-Difluoro-piperidin-1-yl)-[5-(1-isopropyl-piperidin-4-yloxy)-1-(3-methoxy-phenyl)-1H-indol-2-yl]-methanone In analogy to the procedure described for the synthesis of example 6, the title compound was synthesized from (4,4-difluoro-piperidin-1-yl)-[5-(1-isopropyl-piperidin-4-yloxy)-1H-indol-2-yl]-methanone (intermediate 1) and 3-methoxyphenylboronic acid. The title compound was obtained in 90% yield as yellow foam. MS (m/e): 516.2 (MH+, 100%).

Example 16

(4,4-Difluoro-piperidin-1-yl)-[5-(1-isopropyl-piperidin-4-yloxy)-1-(4-trifluoromethyl-phenyl)-1H-indol-2-yl]-methanone In analogy to the procedure described for the synthesis of example 6, the title compound was synthesized from (4,4-difluoro-piperidin-1-yl)-[5-(1-isopropyl-piperidin-4-yloxy)-1H-indol-2-yl]-methanone (intermediate 1) and 4-(trifluoromethyl)phenyl boronic acid. The title compound was obtained in 52% yield as yellow foam. MS (m/e): 550.2 (MH+, 100%).

Example 17

(4,4-Difluoro-piperidin-1-yl)-[5-(1-isopropyl-piperidin-4-yloxy)-1-phenyl-1H-indol-2-yl]-methanone In analogy to the procedure described for the synthesis of example 6, the title compound was synthesized from (4,4-difluoro-piperidin-1-yl)-[5-(1-isopropyl-piperidin-4-yloxy)-1H-indol-2-yl]-methanone (intermediate 1) and phenylboronic acid. The title compound was obtained in 48% yield as white foam. MS (m/e): 482.3 (MH+, 100%).

Example 18

(4,4-Difluoro-piperidin-1-yl)-[5-(1-isopropyl-piperidin-4-yloxy)-1-p-tolyl-1H-indol-2-yl]-methanone In analogy to the procedure described for the synthesis of example 6, the title compound was synthesized from (4,4-difluoro-piperidin-1-yl)-[5-(1-isopropyl-piperidin-4-yloxy)-1H-indol-2-yl]-methanone (intermediate 1) and 4-methylphenylboronic acid. The title compound was obtained in 59% yield as light yellow foam. MS (m/e): 496.1 (MH+, 100%).

Example 19

[1-(4-Chloro-phenyl)-5-(1-isopropyl-piperidin-4-yloxy)-1H-indol-2-yl]-(4,4-difluoro-piperidin-1-yl)-methanone In analogy to the procedure described for the synthesis of example 6, the title compound was synthesized from (4,4-difluoro-piperidin-1-yl)-[5-(1-isopropyl-piperidin-4-yloxy)-1H-indol-2-yl]-methanone (intermediate 1) and 4-chlorophenylboronic acid. The title compound was obtained in 93% yield as light yellow foam. MS (m/e): 516.2 (MH+, 100%).

Example 20

[1-(3,4-Dichloro-phenyl)-5-(1-isopropyl-piperidin-4-yloxy)-1H-indol-2-yl]-(4,4-difluoro-piperidin-1-yl)-methanone In analogy to the procedure described for the synthesis of example 6, the title compound was synthesized from (4,4-difluoro-piperidin-1-yl)-[5-(1-isopropyl-piperidin-4-yloxy)-1H-indol-2-yl]-methanone (intermediate 1) and 3,4-dichlorophenylboronic acid. The title compound was obtained in 81% yield as yellow foam. MS (m/e): 550.2 (MH+, 100%).

Example 21

5-[2-(4,4-Difluoro-piperidine-1-carbonyl)-5-(1-isopropyl-piperidin-4-yloxy)-indol-1-yl]-pyridine-2-carbonitrile In analogy to the procedure described for the synthesis of example 6, the title compound was synthesized from (4,4-difluoro-piperidin-1-yl)-[5-(1-isopropyl-piperidin-4-yloxy)-1H-indol-2-yl]-methanone (intermediate 1) and 2-cyanopyridine-5-boronic acid pinacol ester. The title compound was obtained in 51% yield as yellow foam. MS (m/e): 508.4 (MH+, 100%).

Example 22

(4,4-Difluoro-piperidin-1-yl)-[5-(1-isopropyl-piperidin-4-yloxy)-1-(4-methoxy-phenyl)-1H-indol-2-yl]-methanone In analogy to the procedure described for the synthesis of example 6, the title compound was synthesized from (4,4-difluoro-piperidin-1-yl)-[5-(1-isopropyl-piperidin-4-yloxy)-1H-indol-2-yl]-methanone (intermediate 1) and 4-methoxyphenylboronic acid. The title compound was obtained in 38% yield as yellow foam. MS (m/e): 512.2 (MH+, 100%).

Example 23

3-[2-(4,4-Difluoro-piperidine-1-carbonyl)-5-(1-isopropyl-piperidin-4-yloxy)-indol-1-yl]-benzonitrile In analogy to the procedure described for the synthesis of example 6, the title compound was synthesized from (4,4-difluoro-piperidin-1-yl)-[5-(1-isopropyl-piperidin-4-yloxy)-1H-indol-2-yl]-methanone (Intermediate 1) and 3-cyanophenylboronic acid. The title compound was obtained in 46% yield as yellow foam. MS (m/e): 507.3 (MH+, 100%).

Example 24

4-[2-(4,4-Difluoro-piperidine-1-carbonyl)-5-(1-isopropyl-piperidin-4-yloxy)-indol-1-yl]-benzonitrile In analogy to the procedure described for the synthesis of example 6, the title compound was synthesized from (4,4-difluoro-piperidin-1-yl)-[5-(1-isopropyl-piperidin-4-yloxy)-1H-indol-2-yl]-methanone (intermediate 1) and 4-cyanophenylboronic acid. The title compound was obtained in 45% yield as yellow foam. MS (m/e): 507.4 (MH+, 100%).

Example 25

[5-(1-Isopropyl-piperidin-4-yloxy)-1-phenyl-1H-indol-2-yl]-morpholin-4-yl-methanone In analogy to the procedure described for the synthesis of example 6, the title compound was synthesized from [5-(1-isopropyl-piperidin-4-yloxy)-1H-indol-2-yl]-morpholin-4-yl-methanone (intermediate 2) and phenylboronic acid. The title compound was obtained in 77% yield as yellow foam. MS (m/e): 448.2 (MH+, 100%).

Example 26

[1-(4-Chloro-phenyl)-5-(1-isopropyl-piperidin-4-yloxy)-1H-indol-2-yl]-morpholin-4-yl-methanone In analogy to the procedure described for the synthesis of example 6, the title compound was synthesized from [5-(1-isopropyl-piperidin-4-yloxy)-1H-indol-2-yl]-morpholin-4-yl-methanone (intermediate 2) and 4-chlorophenylboronic acid. The title compound was obtained in 90% yield as yellow foam. MS (m/e): 482.3 (MH+, 100%).

Example 27

[1-(3,4-Dichloro-phenyl)-5-(1-isopropyl-piperidin-4-yloxy)-1H-indol-2-yl]-morpholin-4-yl-methanone In analogy to the procedure described for the synthesis of example 6, the title compound was synthesized from [5-(1-isopropyl-piperidin-4-yloxy)-1H-indol-2-yl]-morpholin-4-yl-methanone (intermediate 2) and 3,4-dichlorobenzeneboronic acid. The title compound was obtained in 90% yield as yellow foam. MS (m/e): 516.2 (MH+, 100%).

Example 28

[5-(1-Isopropyl-piperidin-4-yloxy)-1-p-tolyl-1H-indol-2-yl]-morpholin-4-yl-methanone In analogy to the procedure described for the synthesis of example 6, the title compound was synthesized from [5-(1- isopropyl-piperidin-4-yloxy)-1H-indol-2-yl]-morpholin-4-yl-methanone (intermediate 2) and 4-methylbenzeneboronic acid. The title compound was obtained in 57% yield as a yellow foam. MS (m/e): 462.2 (MH$^+$, 100%).

Example 29

[5-(1-Isopropyl-piperidin-4-yloxy)-1-(4-methoxyphenyl)-1H-indol-2-yl]-morpholin-4-yl-methanone In analogy to the procedure described for the synthesis of example 6, the title compound was synthesized from [5-(1-isopropyl-piperidin-4-yloxy)-1H-indol-2-yl]-morpholin-4-yl-methanone (intermediate 2) and 4-methoxyphenylboronic acid. The title compound was obtained in 56% yield as yellow foam. MS (m/e): 478.2 (MH$^+$, 100%).

Example 30

4-[5-(1-Isopropyl-piperidin-4-yloxy)-2-(morpholine-4-carbonyl)-indol-1-yl]-benzonitrile In analogy to the procedure described for the synthesis of example 6, the title compound was synthesized from [5-(1-isopropyl-piperidin-4-yloxy)-1H-indol-2-yl]-morpholin-4-yl-methanone (intermediate 2) and 4-cyanophenylboronic acid. The title compound was obtained in 31% yield as yellow foam. MS (m/e): 473.2 (MH$^+$, 100%).

Example 31

5-[2-(4,4-Difluoro-piperidine-1-carbonyl)-5-(1-isopropyl-piperidin-4-yloxy)-indol-1-yl]-2-fluoro-benzonitrile In analogy to the procedure described for the synthesis of example 6, the title compound was synthesized from (4,4-difluoro-piperidin-1-yl)-[5-(1-isopropyl-piperidin-4-yloxy)-1H-indol-2-yl]-methanone (intermediate 1) and 3-cyano-4-fluorophenylboronic acid. The title compound was obtained in 22% yield as orange oil. MS (m/e): 525.2 (MH$^+$, 100%).

Example 32

(4,4-Difluoro-piperidin-1-yl)-[5-(1-isopropyl-piperidin-4-yloxy)-1-(2-methoxy-pyrimidin-5-yl)-1H-indol-2-yl]-methanone In analogy to the procedure described for the synthesis of example 6, the title compound was synthesized from (4,4-difluoro-piperidin-1-yl)-[5-(1-isopropyl-piperidin-4-yloxy)-1H-indol-2-yl]-methanone (intermediate 1) and 2-methoxy-5-pyrimidineboronic acid. The title compound was obtained in 9% yield as yellow oil. MS (m/e): 514.3 (MH$^+$, 100%).

Example 33

(4,4-Difluoro-piperidin-1-yl)-[5-(1-isopropyl-piperidin-4-yloxy)-1-thiophen-3-yl-1H-indol-2-yl]-methanone In analogy to the procedure described for the synthesis of example 6, the title compound was synthesized from (4,4-difluoro-piperidin-1-yl)-[5-(1-isopropyl-piperidin-4-yloxy)-1H-indol-2-yl]-methanone (intermediate 1) and 3-thiopheneboronic acid. The title compound was obtained in 5% yield as a yellow oil. MS (m/e): 488.5 (MH$^+$, 100%).

Example 34

(4,4-Difluoro-piperidin-1-yl)-[5-(1-isopropyl-piperidin-4-yloxy)-1-pyrimidin-5-yl-1H-indol-2-yl]-methanone A mixture of (4,4-difluoro-piperidin-1-yl)-[5-(1-isopropyl-piperidin-4-yloxy)-1H-indol-2-yl]-methanone (intermediate 1, 100 mg, 1.0 eq.), 5-bromopyrimidine (44 mg, 1.1 eq.), trans-1,2-diaminocyclohexane (18 mg, 0.65 eq.), copper(I) iodide (6 mg, 0.12 eq.) and potassium phosphate tribasic (110 mg, 2.1 eq.) in dioxan (2.0 mL) was stirred under reflux for 3 d. Potassium carbonate (72 mg, 2.1 eq.) was added and the mixture was refluxed for 1 d, evaporated to dryness and purified on silica gel, eluting with a 49:1:0 to 95:5:0.25 gradient of dichloromethane/methanol/ammonium hydroxide, to yield 121 mg (100%) from the desired product as orange oil. MS (m/e): 484.4 (MH$^+$, 100%).

Example 35

(4,4-Difluoro-piperidin-1-yl)-[5-(1-isopropyl-piperidin-4-yloxy)-1-pyridin-2-yl-1H-indol-2-yl]-methanone In analogy to the procedure described for the synthesis of example 34, the title compound was synthesized from (4,4-difluoro-piperidin-1-yl)-[5-(1-isopropyl-piperidin-4-yloxy)-1H-indol-2-yl]-methanone (intermediate 1) and 2-iodopyridine. The title compound was obtained in 88% yield as an orange oil. MS (m/e): 483.3 (MH$^+$, 100%).

Example 36

(4,4-Difluoro-piperidin-1-yl)-[5-(1-isopropyl-piperidin-4-yloxy)-1-thiophen-2-yl-1H-indol-2-yl]-methanone In analogy to the procedure described for the synthesis of example 34, the title compound was synthesized from (4,4-difluoro-piperidin-1-yl)-[5-(1-isopropyl-piperidin-4-yloxy)-1H-indol-2-yl]-methanone (intermediate 1) and 2-iodothiophene. The title compound was obtained in 51% yield as light brown foam. MS (m/e): 488.4 (MH$^+$, 100%).

Example 37

(4,4-Difluoro-piperidin-1-yl)-[5-(1-isopropyl-piperidin-4-yloxy)-1-(6-morpholin-4-yl-pyridin-3-yl)-1H-indol-2-yl]-methanone In analogy to the procedure described for the synthesis of example 6, the title compound was synthesized from (4,4-difluoro-piperidin-1-yl)-[5-(1-isopropyl-piperidin-4-yloxy)-1H-indol-2-yl]-methanone (intermediate 1) and 2-morpholino-5-pyridine boronic acid. The title compound was obtained in 7% yield as yellow solid. MS (m/e): 568.4 (MH$^+$, 100%).

Example 38

(4,4-Difluoro-piperidin-1-yl)-[5-(1-isopropyl-piperidin-4-yloxy)-1-pyridin-3-yl-1H-indol-2-yl]-methanone In analogy to the procedure described for the synthesis of example 34, the title compound was synthesized from (4,4- difluoro-piperidin-1-yl)-[5-(1-isopropyl-piperidin-4-yloxy)-1H-indol-2-yl]-methanone (intermediate 1) and 3-iodopyridine. The title compound was obtained in 82% yield as light brown foam. MS (m/e): 483.3 (MH+, 100%).

Example 39

[6-Chloro-5-(1-isopropyl-piperidin-4-yloxy)-1-pyrimidin-5-yl-1H-indol-2-yl]-(4,4-difluoro-piperidin-1-yl)-methanone Step 1: 6-Chloro-5-methoxy-1H-indole-2-carboxylic acid ethyl ester Solution A: Sodium nitrite (4.756 g, 1.12 eq) was added to a cold (0° C.) mixture of 3-chloro-p-anisidine (10 g, 1.0 eq) in concentrated hydrochloric acid (15.4 mL, 3.0 eq), water (20 mL) and ice (10 g). Sodium acetate (5.554 g, 1.1 eq) was added to adjust the pH to 3.
Solution B: Potassium hydroxide (4.417 g, 1.1 eq) was dissolved in water (5 mL) and added to a solution of ethyl-2-methylacetoacetate (9.6 mL, 1.1 eq) in ethanol (45 mL).
Solution A was added to solution B at 0° C. and the mixture was stirred in the ice bath for 2 h, extracted with ethyl acetate, washed with a 10% sodium bicarbonate solution and brine, dried over sodium sulfate and concentrated in vacuo to yield 15.073 g red oil.
This red oil was dissolved in hydrochloric acid 3N in ethanol (223 mL, 14.0 eq) and stirred under reflux for 3 h. The reaction mixture was partitionned between ethyl acetate and water. The aqueous layer was extracted twice with ethyl acetate and the combined organic fractions were washed with 10% sodium bicarbonate solution and brine, dried over sodium sulfate, filtered and concentrated in vacuo to afford 12.1 g dark brown liquid.
This brown liquid was dissolved in chloroform (100 mL) under nitrogen atmosphere and boron trifluoride ethyl etherate (5.61 mL, 1.0 eq) was added. The mixture was refluxed for 20 h, then partitionned between dichloromethane and 10% sodium bicarbonate solution. The aqueous layer was extracted twice with dichloromethane and the combined organic fractions were washed with 10% sodium bicarbonate solution and brine, dried over sodium sulfate, filtered, evaporated to dryness and purified on silica gel, eluting with a 2:1 to 1:2 gradient of cyclohexane/dichloromethane, to yield 990 mg (6%) from the desired product as orange solid. MS (m/e): 253.1 (M+, 70%).

Step 2: 6-Chloro-5-hydroxy-1H-indole-2-carboxylic acid ethyl ester

To a cooled (−78° C.) solution of 6-chloro-5-methoxy-1H-indole-2-carboxylic acid ethyl ester (example 39, step 1, 930 mg, 1.0 eq.) in dichloromethane (20 mL), was slowly added a solution of boron tribromide 1M in dichloromethane (7.33 mL, 2.0 eq.). The mixture was stirred at room temperature for 1 h, partitionned between ethyl acetate and ice water. The aqueous layer was extracted with ethyl acetate and the combined organic fractions were washed with 10% sodium bicarbonate solution and brine, dried over sodium sulfate, filtered, evaporated to dryness and purified on silica gel, eluting with a 4:1 to 3:1 gradient of cyclohexane/ethyl acetate, to yield 655 mg (74%) from the desired product as light brown solid. MS (m/e): 239.2 (M+, 35%).

Step 3: 6-Chloro-5-(1-isopropyl-piperidin-4-yloxy)-1H-indole-2-carboxylic acid ethyl ester In analogy to the procedure described for the synthesis of intermediate 1, step 2, the title compound was synthesized from 6-chloro-5-hydroxy-1H-indole-2-carboxylic acid ethyl ester (example 39, step 2). The title compound was obtained in 66% yield as light yellow foam. MS (m/e): 365.0 (MH+, 100%).

Step 4: 6-Chloro-5-(1-isopropyl-piperidin-4-yloxy)-1H-indole-2-carboxylic acid hydrochloride salt with 1 eq. lithium chloride In analogy to the procedure described for the synthesis of intermediate 1, step 3, the title compound was synthesized from 6-chloro-5-(1-isopropyl-piperidin-4-yloxy)-1H-indole-2-carboxylic acid ethyl ester (example 39, step 3). The title compound was obtained in quant. yield as yellow solid. MS (m/e): 337.0 (MH+, 100%).

Step 5: [6-chloro-5-(1-isopropyl-piperidin-4-yloxy)-1H-indol-2-yl]-(4,4-difluoro-piperidin-1-yl)-methanone In analogy to the procedure described for the synthesis of intermediate 1, step 4, the title compound was synthesized from 6-chloro-5-(1-isopropyl-piperidin-4-yloxy)-1H-indole-2-carboxylic acid hydrochloride salt with 1 eq. lithium chloride (example 39, step 4). The title compound was obtained in 70% yield as light yellow solid. MS (m/e): 440.3 (MH+, 100%).

Step 6: [6-Chloro-5-(1-isopropyl-piperidin-4-yloxy)-1-pyrimidin-5-yl-1H-indol-2-yl]-(4,4-difluoro-piperidin-1-yl)-methanone In analogy to the procedure described for the synthesis of example 34, the title compound was synthesized from [6-chloro-5-(1-isopropyl-piperidin-4-yloxy)-1H-indol-2-yl]-(4,4-difluoro-piperidin-1-yl)-methanone (example 39, step 5). The title compound was obtained in 53% yield as yellow foam. MS (m/e): 518.2 (MH+, 100%).

Example 40

[6-Chloro-5-(1-isopropyl-piperidin-4-yloxy)-1-pyrimidin-5-yl-1H-indol-2-yl]-(4-hydroxy-4-methyl-piperidin-1-yl)-methanone Step 1: [6-Chloro-5-(1-isopropyl-piperidin-4-yloxy)-1H-indol-2-yl]-(4-hydroxy-4-methyl-piperidin-1-yl)-methanone In analogy to the procedure described for the synthesis of intermediate 1, step 4, the title compound was synthesized from 6-chloro-5-(1-isopropyl-piperidin-4-yloxy)-1H-indole-2-carboxylic acid hydrochloride salt with 1 eq. lithium chloride (example 39, step 4) and 4-methyl-piperidin-4-ol (CAS Nr. 3970-68-1). The title compound was obtained in 72% yield as yellow foam. MS (m/e): 434.3 (MH+, 100%).

Step 2: [6-Chloro-5-(1-isopropyl-piperidin-4-yloxy)-1-pyrimidin-5-yl-1H-indol-2-yl]-(4-hydroxy-4-methyl-piperidin-1-yl)-methanone In analogy to the procedure described for the synthesis of example 34, the title compound was synthesized from [6-chloro-5-(1-isopropyl-piperidin-4-yloxy)-1H-indol-2-yl]-(4-hydroxy-4-methyl-piperidin-1-yl)-methanone (example 40, step 1). The title compound was obtained in 47% yield as orange foam. MS (m/e): 512.3 (MH+, 100%).

Example 41

[6-Bromo-1-(2-chloro-pyridin-4-yl)-5-(1-isopropyl-piperidin-4-yloxy)-1H-indol-2-yl]-morpholin-4-yl-methanone Step 1: 3-Bromo-4-methoxy-phenylamine Stannous chloride (96.839 g, 5.0 eq.) was added to a solution of 2-bromo-4-nitroanisole (23.7 g, 1.0 eq.) in ethanol (250 mL) and the mixture was stirred at 70° C. for 2 h, partitioned between ethyl acetate and sodium bicarbonate solution 10%. The pH was adjusted to 9 with 1N sodium hydroxide solution and the aqueous layer was extracted twice with ethyl acetate. The combined organic fractions were washed with water and brine, dried over magnesium sulfate, filtered, evaporated to dryness and purified on silica gel, eluting with hexane/ethyl acetate 1:1, to yield 13.82 g (67%) from the desired product as light brown solid. MS (m/e): 204.1 ($MH^+$, 100%).

Step 2: 6-Bromo-5-methoxy-1H-indole-2-carboxylic acid ethyl ester

In analogy to the procedure described for the synthesis of example 39, step 1, the title compound was synthesized from 3-bromo-4-methoxy-phenylamine (example 41, step 1). The title compound was obtained in 12% yield as light yellow solid. MS (m/e): 299.0 ($MH^+$, 95%).

Step 3: 6-Bromo-5-hydroxy-1H-indole-2-carboxylic acid ethyl ester

In analogy to the procedure described for the synthesis of example 39, step 2, the title compound was synthesized from 6-bromo-5-methoxy-1H-indole-2-carboxylic acid ethyl ester (example 41, step 2). The title compound was obtained in 79% yield as light yellow solid. MS (m/e): 282.2 (M-H, 100%).

Step 4: 6-Bromo-5-(1-isopropyl-piperidin-4-yloxy)-1H-indole-2-carboxylic acid ethyl ester In analogy to the procedure described for the synthesis of intermediate 1, step 2, the title compound was synthesized from 6-bromo-5-hydroxy-1H-indole-2-carboxylic acid ethyl ester (example 41, step 3). The title compound was obtained in 56% yield as light yellow solid. MS (m/e): 409.0 ($MH^+$, 100%).

Step 5: 6-Bromo-5-(1-isopropyl-piperidin-4-yloxy)-1H-indole-2-carboxylic acid hydrochloride salt with 1 eq. lithium chloride In analogy to the procedure described for the synthesis of intermediate 1, step 3, the title compound was synthesized from 6-bromo-5-(1-isopropyl-piperidin-4-yloxy)-1H-indole-2-carboxylic acid ethyl ester (example 41, step 4). The title compound was obtained in quant. yield as light yellow solid. MS (m/e): 381.0 ($MH^+$, 100%).

Step 6: [6-Bromo-5-(1-isopropyl-piperidin-4-yloxy)-1H-indol-2-yl]-morpholin-4-yl-methanone In analogy to the procedure described for the synthesis of intermediate 1, step 4, the title compound was synthesized from 6-bromo-5-(1-isopropyl-piperidin-4-yloxy)-1H-indole-2-carboxylic acid hydrochloride salt with 1 eq. lithium chloride (example 41, step 5) and morpholine. The title compound was obtained in 75% yield as light yellow solid. MS (m/e): 450.1 ($MH^+$, 100%).

Step 7: [6-Bromo-1-(2-chloro-pyridin-4-yl)-5-(1-isopropyl-piperidin-4-yloxy)-1H-indol-2-yl]-morpholin-4-yl-methanone In analogy to the procedure described for the synthesis of example 6, the title compound was synthesized from [6-bromo-5-(1-isopropyl-piperidin-4-yloxy)-1H-indol-2-yl]-morpholin-4-yl-methanone (example 41, step 6) and 2-chloropyridine-4-boronic acid. The title compound was obtained in 12% yield as light yellow oil. MS (m/e): 561.4 ($MH^+$, 100%).

Example 42

[6-Bromo-1-(2-chloro-pyridin-4-yl)-5-(1-isopropyl-piperidin-4-yloxy)-1H-indol-2-yl]-(4,4-difluoro-piperidin-1-yl)-methanone Step 1: [6-Bromo-5-(1-isopropyl-piperidin-4-yloxy)-1H-indol-2-yl]-(4,4-difluoro-piperidin-1-yl)-methanone In analogy to the procedure described for the synthesis of intermediate 1, step 4, the title compound was synthesized from 6-bromo-5-(1-isopropyl-piperidin-4-yloxy)-1H-indole-2-carboxylic acid hydrochloride salt with 1 eq. lithium chloride (example 41, step 5). The title compound was obtained in 77% yield as light yellow solid. MS (m/e): 486.2 ($MH^+$, 100%).

Step 2: [6-Bromo-1-(2-chloro-pyridin-4-yl)-5-(1-isopropyl-piperidin-4-yloxy)-1H-indol-2-yl]-(4,4-difluoro-piperidin-1-yl)-methanone In analogy to the procedure described for the synthesis of example 6, the title compound was synthesized from [6-bromo-5-(1-isopropyl-piperidin-4-yloxy)-1H-indol-2-yl]-(4,4-difluoro-piperidin-1-yl)-methanone (example 42, step 1) and 2-chloropyridine-4-boronic acid. The title compound was obtained in 20% yield as light yellow oil. MS (m/e): 595.1 ($MH^+$, 100%).

Example 43

[5-(1-Cyclobutyl-piperidin-4-yloxy)-1-pyrimidin-5-yl-1H-indol-2-yl]-(4,4-difluoro-piperidin-1-yl)-methanone Step 1: 4-(3-Methyl-4-nitro-phenoxy)-piperidine-1-carboxylic acid tert-butyl ester Diisopropyl azodicarboxylate (10.56 mL, 1.6 eq.) was added to a cold (0° C.) mixture of 3-methyl-4-nitrophenol (5 g, 1.0 eq.), 1-tert-butyloxycarbonyl-4-hydroxy-piperidine (9.96 g, 1.6 eq.) and triphenylphosphine (13.85 g, 1.6 eq.) in tetrahydrofuran (205 mL). After 1 h stirring, the mixture was evaporated to dryness and dissolved in tert-butylmethylether. The organic phase was washed with 0.5M sodium hydroxide solution and 5% sodium chloride solution, dried over sodium sulfate, filtered and evaporated to dryness. The product was recrystallized from methanol to yield 9.498 g (88%) as white crystals. MS (m/e): 336.2 (M, 10%).

Step 2: 4-[3-(2-Ethoxycarbonyl-2-oxo-ethyl)-4-nitro-phenoxy]-piperidine-1-carboxylic acid tert-butyl ester A solution of 4-(3-methyl-4-nitro-phenoxy)-piperidine-1-carboxylic acid tert-butyl ester (example 43, step 1, 41.9 g, 1.0 eq.) and diethyloxalate (18.77 mL, 1.1 eq.) in tetrahydrofuran (241.7 mL) was dropped into a cold (0-5° C.) solution of potassium tert-butylate (28.54 g, 2.0 eq.) and ethanol (43.64 mL, 6.0 eq.) in tetrahydrofuran (1.022 L). The mixture was stirred for 3 h at 0-5° C. and for 18.5 h at room temperature, poured into 1M hydrochloric acid solution. The aqueous phase was extracted 3 times with tert-butylmethylether and the combined organic phases were washed with brine, dried over sodium sulfate, filtered, evaporated to dryness in vacuo and crystallized from ethanol to yield 44.09 g (81%) as white crystals. MS (m/e): 436.2 (M, 5%).

Step 3: 5-(1-tert-Butoxycarbonyl-piperidin-4-yloxy)-1H-indole-2-carboxylic acid ethyl ester A mixture of 4-[3-(2-ethoxycarbonyl-2-oxo-ethyl)-4-nitro-phenoxy]-piperidine-1-carboxylic acid tert-butyl ester (example 43, step 2, 42.25 g, 1.0 eq.), palladium on activated charcoal (10%, 2.111 g, 0.02 eq.) in ethanol (950 mL) was hydrogenated at 30° C. for 9 h. The mixture was filtered, washed with ethanol and evaporated to dryness. The product was recrystallized from ethyl acetate and heptane to yield 25.998 g (69%) as white crystals. MS (m/e): 388.2 (M, 45%).

Step 4: 5-(1-tert-Butoxycarbonyl-piperidin-4-yloxy)-1H-indole-2-carboxylic acid hydrochloride salt with 1 eq. lithium chloride In analogy to the procedure described for the synthesis of intermediate 1, step 3, the title compound was synthesized from 5-(1-tert-butoxycarbonyl-piperidin-4-yloxy)-1H-indole-2-carboxylic acid ethyl ester (example 43, step 3). The title compound was obtained in 100% yield as light brown solid. MS (m/e): 359.2 (M-H, 100%).

Step 5: 4-[2-(4,4-Difluoro-piperidine-1-carbonyl)-1H-indol-5-yloxy]-piperidine-1-carboxylic acid tert-butyl ester In analogy to the procedure described for the synthesis of intermediate 1, step 4, the title compound was synthesized from 5-(1-tert-butoxycarbonyl-piperidin-4-yloxy)-1H-indole-2-carboxylic acid hydrochloride salt with 1 eq. lithium chloride (example 43, step 4). The title compound was obtained in 59% yield as white solid. MS (m/e): 464.3 (MH$^+$, 75%).

Step 6: (4,4-Difluoro-piperidin-1-yl)-[5-(piperidin-4-yloxy)-1H-indol-2-yl]-methanone Trifluoroacetic acid (4.13 mL, 10.0 eq.) was added to a cold (0° C.) solution of 4-[2-(4,4-difluoro-piperidine-1-carbonyl)-1H-indol-5-yloxy]-piperidine-1-carboxylic acid tert-butyl ester (example 43, step 5, 2.5 g, 1.0 eq.) in dichloromethane (20 mL). The mixture was stirred for 1 h at room temperature, evaporated to dryness and purified on silica gel, eluting with dichloromethane/methanol/ammonium hydroxide 95:5:0.25, to yield 1.7 g (86%) from the desired product as white solid. MS (m/e): 364.4 (MH$^+$, 100%).

Step 7: [5-(1-Cyclobutyl-piperidin-4-yloxy)-1H-indol-2-yl]-(4,4-difluoro-piperidin-1-yl)-methanone A mixture of (4,4-difluoro-piperidin-1-yl)-[5-(piperidin-4-yloxy)-1H-indol-2-yl]-methanone (example 43, step 6, 350 mg, 1.0 eq.), acetic acid (0.17 mL, 3.0 eq.) and cyclobutanone (138 mg, 2.0 eq.) in tetrahydrofuran (6 mL) was stirred at 55° C. for 1 h. At room temperature, sodium acetoxyborohydride (421 mg, 2.0 eq.) was added and the mixture stirred for 16 h at 65° C. The reaction mixture was partitionned between ethyl acetate and water. The aqueous layer was extracted twice with ethyl acetate and the combined organic fractions were washed twice with saturated sodium bicarbonate solution, dried over sodium sulfate, filtered, evaporated to dryness and purified on silica gel, eluting with a 49:1:0 to 95:5:0.25 gradient of dichloromethane/methanol/ammonium hydroxide, to yield 265 mg (65%) from the desired product as off-white solid. MS (m/e): 418.1 (MH$^+$, 100%).

Step 8: [5-(1-Cyclobutyl-piperidin-4-yloxy)-1-pyrimidin-5-yl-1H-indol-2-yl]-(4,4-difluoro-piperidin-1-yl)-methanone In analogy to the procedure described for the synthesis of example 34, the title compound was synthesized from [5-(1-cyclobutyl-piperidin-4-yloxy)-1H-indol-2-yl]-(4,4-difluoro-piperidin-1-yl)-methanone (example 43, step 7). The title compound was obtained in 73% yield as white foam. MS (m/e): 496.4 (MH$^+$, 100%).

Example 44

(4-Hydroxy-4-methyl-piperidin-1-yl)-[5-(1-isopropyl-piperidin-4-yloxy)-1-pyrimidin-5-yl-1H-indol-2-yl]-methanone

Step 1: 5-(1-tert-Butoxycarbonyl-piperidin-4-yloxy)-1-pyrimidin-5-yl-1H-indole-2-carboxylic acid ethyl ester In analogy to the procedure described for the synthesis of example 34, the title compound was synthesized from 5-(1-tert-butoxycarbonyl-piperidin-4-yloxy)-1H-indole-2-carboxylic acid ethyl ester (example 43, step 3). The title compound was obtained in 63% yield as off-white solid. MS (m/e): 467.3 (MH$^+$, 45%).

Step 2: 5-(Piperidin-4-yloxy)-1-pyrimidin-5-yl-1H-indole-2-carboxylic acid ethyl ester In analogy to the procedure described for the synthesis of example 43, step 6, the title compound was synthesized from 5-(1-tert-butoxycarbonyl-piperidin-4-yloxy)-1-pyrimidin-5-yl-1H-indole-2-carboxylic acid ethyl ester (example 44, step 1). The title compound was obtained in quant. yield as off-white solid. MS (m/e): 367.0 (MH$^+$, 100%).

Step 3: 5-(1-Isopropyl-piperidin-4-yloxy)-1-pyrimidin-5-yl-1H-indole-2-carboxylic acid ethyl ester In analogy to the procedure described for the synthesis of example 43, step 7, the title compound was synthesized from 5-(piperidin-4-yloxy)-1-pyrimidin-5-yl-1H-indole-2-carboxylic acid ethyl ester (example 44, step 2) and acetone. The title compound was obtained in 46% yield as light brown foam. MS (m/e): 409.4 (MH$^+$, 100%).

Step 4: 5-(1-Isopropyl-piperidin-4-yloxy)-1-pyrimidin-5-yl-1H-indole-2-carboxylic acid hydrochloride salt with 1 eq. lithium chloride In analogy to the procedure described for the synthesis of intermediate 1, step 3, the title compound was synthesized from 5-(1-isopropyl-piperidin-4-yloxy)-1-pyrimidin-5-yl-1H-indole-2-carboxylic acid ethyl ester (example 44, step 3). The title compound was obtained in 100% yield as white solid. MS (m/e): 381.1 (MH$^+$, 100%).

Step 5: (4-Hydroxy-4-methyl-piperidin-1-yl)-[5-(1-isopropyl-piperidin-4-yloxy)-1-pyrimidin-5-yl-1H-indol-2-yl]-methanone In analogy to the procedure described for the synthesis of intermediate 1, step 4, the title compound was synthesized from 5-(1-isopropyl-piperidin-4-yloxy)-1-pyrimidin-5-yl-1H-indole-2-carboxylic acid hydrochloride salt with 1 eq. lithium chloride (example 44, step 4) and 4-methyl-piperidin-4-ol (CAS Nr. 3970-68-1). The title compound was obtained in 66% yield as light brown foam. MS (m/e): 478.2 (MH$^+$, 100%).

Example 45

[5-(1-Cyclobutyl-piperidin-4-yloxy)-1-pyrimidin-5-yl-1H-indol-2-yl]-(4-hydroxy-4-methyl-piperidin-1-yl)-methanone Step 1: 5-(1-Cyclobutyl-piperidin-4-yloxy)-1-pyrimidin-5-yl-1H-indole-2-carboxylic acid ethyl ester In analogy to the procedure described for the synthesis of example 43, step 7, the title compound was synthesized from 5-(piperidin-4-yloxy)-1-pyrimidin-5-yl-1H-indole-2-carboxylic acid ethyl ester (example 44, step 2) and cyclobutanone. The title compound was obtained in 58% yield as light yellow solid. MS (m/e): 421.1 (MH$^+$, 100%).

Step 2: 5-(1-Cyclobutyl-piperidin-4-yloxy)-1-pyrimidin-5-yl-1H-indole-2-carboxylic acid hydrochloride salt with 1 eq. lithium chloride In analogy to the procedure described for the synthesis of intermediate 1, step 3, the title compound was synthesized from 5-(1-cyclobutyl-piperidin-4-yloxy)-1-pyrimidin-5-yl-1H-indole-2-carboxylic acid ethyl ester (example 45, step 1). The title compound was obtained in quant. yield as white solid. MS (m/e): 391.2 (M-H, 100%).

Step 3: [5-(1-Cyclobutyl-piperidin-4-yloxy)-1-pyrimidin-5-yl-1H-indol-2-yl]-(4-hydroxy-4-methyl-piperidin-1-yl)-methanone In analogy to the procedure described for the synthesis of intermediate 1, step 4, the title compound was synthesized from 5-(1-cyclobutyl-piperidin-4-yloxy)-1-pyrimidin-5-yl-1H-indole-2-carboxylic acid hydrochloride salt with 1 eq. lithium chloride (example 45, step 2) and 4-methyl-piperidin-4-ol (CAS Nr. 3970-68-1). The title compound was obtained in 53% yield as off-white foam. MS (m/e): 490.3 (MH$^+$, 100%).

Example 46

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titanium dioxide | 0.8 mg | 1.6 mg |

The active ingredient is sieved and mixed with microcrystalline cellulose and the mixture is granulated with a solution of polyvinylpyrrolidone in water. The granulate is mixed with sodium starch glycolate and magnesium stearate and compressed to yield kernels of 120 or 350 mg respectively. The kernels are lacquered with an aqueous solution/suspension of the above mentioned film coat.

Example 47

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example 48

Injection solutions can have the following composition:

| | |
|---|---|
| Compound of formula (I) | 3.0 mg |
| Gelatin | 150.0 mg |
| Phenol | 4.7 mg |
| Sodium carbonate | to obtain a final pH of 7 |
| Water for injection solutions | ad 1.0 ml |

Example 49

Soft gelatin capsules containing the following ingredients can be manufactured in a conventional manner:

| Capsule contents | |
|---|---|
| Compound of formula (I) | 5.0 mg |
| Yellow wax | 8.0 mg |

-continued

| | |
|---|---|
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titanium dioxide | 0.4 mg |
| Iron oxide (yellow) | 1.1 mg |

The active ingredient is dissolved in a warm melting of the other ingredients and the mixture is filled into soft gelatin capsules of appropriate size. The filled soft gelatin capsules are treated according to the usual procedures.

Example 50

Sachets containing the following ingredients can be manufactured in a conventional manner:

| | |
|---|---|
| Compound of formula (I) | 50.0 mg |
| Lactose, fine powder | 1015.0 mg |
| Microcrystalline cellulose (AVICEL PH 102) | 1400.0 mg |
| Sodium carboxymethyl cellulose | 14.0 mg |
| Polyvinylpyrrolidone K 30 | 10.0 mg |
| Magnesium stearate | 10.0 mg |
| Flavoring additives | 1.0 mg |

The active ingredient is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

It is to be understood that the invention is not limited to the particular embodiments of the invention described above, as variations of the particular embodiments may be made and still fall within the scope of the appended claims.

What is claimed is:
1. A compound of formula I,

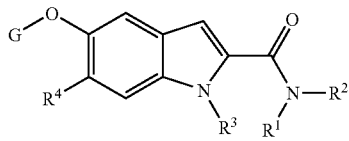

wherein:
$R^1$ is selected from the group consisting of
lower alkyl, lower alkenyl, lower alkynyl,
cycloalkyl, lower cycloalkylalkyl,
lower hydroxyalkyl,
lower alkoxyalkyl,
lower alkylsulfanylalkyl,
lower dialkylaminoalkyl,
lower dialkylcarbamoylalkyl,
phenyl unsubstituted or substituted with one or two groups independently selected from lower alkyl, lower halogenoalkoxy and lower hydroxyalkyl,
lower phenylalkyl wherein the phenyl ring may be unsubstituted or substituted with one or two groups independently selected from lower alkyl, halogen, lower alkoxy and lower hydroxyalkyl,
lower heteroarylalkyl wherein the heteroaryl ring may be unsubstituted or substituted with one or two groups independently selected from lower alkyl, halogen, lower alkoxy and lower hydroxyalkyl and
lower heterocyclylalkyl wherein the heterocyclyl ring may be unsubstituted or substituted with one or two lower alkyl groups;
$R^2$ is selected from the group consisting of hydrogen,
lower alkyl, lower alkenyl, lower alkynyl,
cycloalkyl, lower cycloalkylalkyl,
lower hydroxyalkyl, lower alkoxyalkyl,
lower alkylsulfanylalkyl,
lower dialkylaminoalkyl,
lower dialkylcarbamoylalkyl,
phenyl unsubstituted or substituted with one or two groups independently selected from lower alkyl, lower halogenoalkoxy and lower hydroxyalkyl,
lower phenylalkyl wherein the phenyl ring may be unsubstituted or substituted with one or two groups independently selected from lower alkyl, halogen, lower alkoxy and lower hydroxyalkyl,
lower heteroarylalkyl wherein the heteroaryl ring may be unsubstituted or substituted with one or two groups independently selected from lower alkyl, halogen, lower alkoxy and lower hydroxyalkyl and
lower heterocyclylalkyl wherein the heterocyclyl ring may be unsubstituted or substituted with one or two lower alkyl groups; or
$R^1$ and $R^2$ together with the nitrogen atom to which they are attached form a 4-, 5-, 6- or 7-membered saturated or partly unsaturated heterocyclic ring optionally containing a further heteroatom selected from nitrogen, oxygen or sulfur,
said saturated or partly unsaturated heterocyclic ring
being unsubstituted or substituted by one, two or three groups independently selected from lower alkyl, halogen, halogenoalkyl, hydroxy, lower hydroxyalkyl, lower alkoxy, oxo, phenyl, benzyl, pyridyl and carbamoyl, or
being condensed with a phenyl ring, said phenyl ring being unsubstituted or substituted by one, two or three groups independently selected from lower alkyl, lower alkoxy and halogen;
$R^3$ is selected from the group consisting of lower hydroxyalkyl,
lower cyanoalkyl, lower alkoxycarbonyl,
phenylsulfonyl wherein the phenyl ring may be unsubstituted or substituted with one or two groups independently selected from lower alkyl, halogen, cyano, lower halogenoalkyl, lower alkoxy, lower halogenoalkoxy and lower hydroxyalkyl;
phenyl unsubstituted or substituted with one or two groups independently selected from lower alkyl, halogen, lower halogenoalkyl, cyano, lower alkoxy, lower halogenoalkoxy and lower hydroxyalkyl;
lower phenylalkyl, wherein the phenyl ring may be unsubstituted or substituted with one or two groups independently selected from lower alkyl, halogen, lower halogenoalkyl, cyano, lower alkoxy, lower halogenoalkoxy and lower hydroxyalkyl; and
heteroaryl unsubstituted or substituted with one or two groups independently selected from lower alkyl, lower alkoxy, halogen, lower halogenoalkyl, lower halogenoalkoxy, morpholino and cyano;
R⁴ is hydrogen or halogen;
G is a group selected from

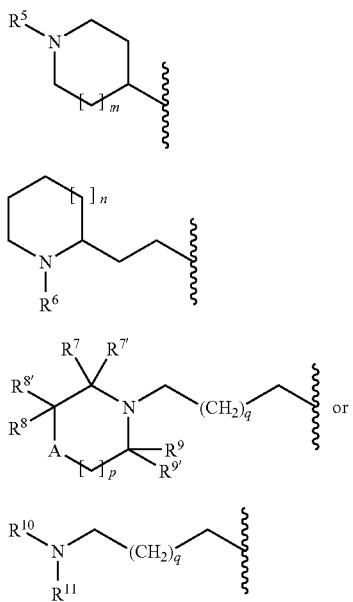

G1

G2

G3

G4 wherein
m is 0, 1 or 2;
R⁵ is selected from lower alkyl, lower halogenoalkyl, cycloalkyl, halogenocycloalkyl, lower cycloalkylalkyl and lower phenylalkyl;
n is 0, 1 or 2;
R⁶ is lower alkyl;
p is 0, 1 or 2;
q is 0, 1 or 2;
A is selected from CR¹²R¹²', O and S;
R⁷, R⁷', R⁸, R⁸', R⁹, R⁹', R¹² and R¹²' independently from each other are selected from the group consisting of hydrogen, lower alkyl, hydoxy, halogen and dialkylamino, or
R⁸ and R¹² together form a double bond;
R¹⁰ is lower alkyl;
R¹¹ is C₃-C₆-alkyl;
and pharmaceutically acceptable salts thereof.

2. The compound according to claim 1, wherein R¹ and R² together with the nitrogen atom to which they are attached form a 4-, 5-, 6- or 7-membered saturated or partly unsaturated heterocyclic ring optionally containing a further heteroatom selected from nitrogen, oxygen or sulfur, said saturated or partly unsaturated heterocyclic ring being unsubstituted or substituted by one, two or three groups independently selected from lower alkyl, halogen, halogenoalkyl, hydroxy, lower hydroxyalkyl, lower alkoxy, oxo, phenyl, benzyl, pyridyl and carbamoyl, or being condensed with a phenyl ring, said phenyl ring being unsubstituted or substituted by one, two or three groups independently selected from lower alkyl, lower alkoxy and halogen.

3. The compound according to claim 1, wherein R¹ and R² together with the nitrogen atom to which they are attached form a heterocyclic ring selected from the group consisting of morpholine, piperidine, 2,5-dihydropyrrole, pyrrolidine, azepane, piperazine, azetidine, thiomorpholine and 3,6-dihydro-2H-pyridine, said heterocyclic ring being unsubstituted or substituted by one, two or three groups independently selected from lower alkyl, halogen, halogenoalkyl, hydroxy, lower alkoxy, oxo, phenyl, benzyl, pyridyl and carbamoyl, or being condensed with a phenyl ring, said phenyl ring being unsubstituted or substituted by one, two or three groups independently selected from lower alkyl, lower alkoxy and halogen.

4. The compound according to claim 1, wherein R¹ and R² together with the nitrogen atom to which they are attached form a heterocyclic ring selected from the group consisting of morpholine, piperidine, 4,4-difluoropiperidine and pyrrolidine.

5. The compound according to claim 1, wherein R¹ is selected from the group consisting of
lower alkyl, lower alkenyl, lower alkynyl,
cycloalkyl, lower cycloalkylalkyl,
lower hydroxyalkyl, lower alkoxyalkyl,
lower alkylsulfanylalkyl,
lower dialkylaminoalkyl, lower dialkylcarbamoylalkyl,
phenyl unsubstituted or substituted with one or two groups independently selected from lower alkyl, lower halogenoalkoxy or lower hydroxyalkyl,
lower phenylalkyl wherein the phenyl ring may be unsubstituted or substituted with one or two groups independently selected from lower alkyl, halogen, lower alkoxy or lower hydroxyalkyl, lower heteroarylalkyl wherein the heteroaryl ring may be unsubstituted or substituted with one or two groups independently selected from lower alkyl, halogen, lower alkoxy or lower hydroxyalkyl and
lower heterocyclylalkyl wherein the heterocyclyl ring may be unsubstituted or substituted with one or two lower alkyl groups and
R² is hydrogen or lower alkyl.

6. The compound according to claim 1, wherein R³ is selected from the group consisting of
lower cyanoalkyl, lower alkoxycarbonyl,
phenylsulfonyl, wherein the phenyl ring may be unsubstituted or substituted with one or two groups independently selected from lower alkyl, halogen, cyano, lower halogenoalkyl, lower alkoxy, lower halogenoalkoxy and lower hydroxyalkyl;
phenyl unsubstituted or substituted with one or two groups independently selected from lower alkyl, halogen, lower halogenoalkyl, cyano, lower alkoxy, lower halogenoalkoxy and lower hydroxyalkyl;
lower phenylalkyl, wherein the phenyl ring may be unsubstituted or substituted with one or two groups independently selected from lower alkyl, halogen, lower halogenoalkyl, cyano, lower alkoxy, lower halogenoalkoxy and lower hydroxyalkyl; and
heteroaryl unsubstituted or substituted with one or two groups independently selected from lower alkyl, lower alkoxy, halogen, lower halogenoalkyl, lower halogenoalkoxy, morpholino and cyano.

7. The compound according to claim 1, wherein R³ is lower cyanoalkyl or lower alkoxycarbonyl.

8. The compound according to claim 1, wherein R³ is phenylsulfonyl, wherein the phenyl ring may be unsubstituted or substituted with one or two groups independently selected from lower alkyl, halogen, cyano, lower halogenoalkyl, lower alkoxy, lower halogenoalkoxy and lower hydroxyalkyl.

9. The compound according to claim 1, wherein R³ is lower phenylalkyl, wherein the phenyl ring may be unsubstituted or substituted with one or two groups independently selected from lower alkyl, halogen, lower halogenoalkyl, cyano, lower alkoxy, lower halogenoalkoxy and lower hydroxyalkyl.

10. The compound according to claim 1, wherein $R^3$ is phenyl unsubstituted or substituted with one or two groups independently selected from lower alkyl, halogen, lower halogenoalkyl, cyano, lower alkoxy, lower halogenoalkoxy and lower hydroxyalkyl.

11. The compound according to claim 1, wherein $R^3$ is heteroaryl unsubstituted or substituted with one or two groups independently selected from lower alkyl, lower alkoxy, halogen, lower halogenoalkyl, lower halogenoalkoxy and cyano.

12. The compound according to claim 11, wherein $R^3$ is a heteroaryl group selected from pyridyl, pyrimidinyl, furanyl and thienyl.

13. The compound according to claim 1, wherein $R^4$ is hydrogen.

14. The compound according to claim 1, wherein G signifies

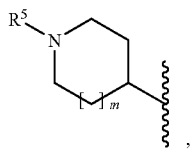

G1

, wherein m is 0, 1 or 2 and $R^5$ is selected from lower alkyl, cycloalkyl, lower cycloalkylalkyl and lower phenylalkyl.

15. The compound according to claim 1, wherein $R^5$ is lower alkyl.

16. The compound according to claim 1, wherein G signifies

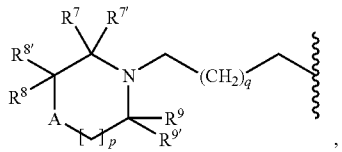

G3

, wherein p is 0, 1 or 2, q is 0, 1 or 2, A is selected from $CR^{12}R^{12'}$, O and S and $R^7$, $R^{7'}$, $R^8$, $R^{8'}$, $R^9$, $R^{9'}$, $R^{12}$ and $R^{12'}$ independently from each other are selected from the group consisting of hydrogen, lower alkyl, hydoxy, halogen and dialkylamino, or $R^8$ and $R^{12}$ together form a double bond.

17. The compound according to claim 16, wherein A is $CR^{12}R^{12'}$, p is 0, q is 1 and $R^7$, $R^{7'}$, $R^8$, $R^{8'}$, $R^9$, $R^{9'}$, $R^{12}$ and $R^{12'}$ independently from each other are selected from hydrogen or lower alkyl.

18. The compound according to claim 1, selected from the group consisting of
- (4,4-difluoro-piperidin-1-yl)-[1-(4-fluoro-benzenesulfonyl)-5-(1-isopropyl-piperidin-4-yloxy)-1H-indol-2-yl]-methanone,
- [1-benzyl-5-(1-isopropyl-piperidin-4-yloxy)-1H-indol-2-yl]-morpholin-4-yl-methanone,
- (4,4-difluoro-piperidin-1-yl)-[1-(4-fluoro-benzyl)-5-(1-isopropyl-piperidin-4-yloxy)-1H-indol-2-yl]-methanone,
- 2-(4,4-difluoro-piperidine-1-carbonyl)-5-(1-isopropyl-piperidin-4-yloxy)-indole-1-carboxylic acid methyl ester,
- [2-(4,4-difluoro-piperidine-1-carbonyl)-5-(1-isopropyl-piperidin-4-yloxy)-indol-1-yl]-acetonitrile,
- [1-(3,5-difluoro-phenyl)-5-(1-isopropyl-piperidin-4-yloxy)-1H-indol-2-yl]-(4,4-difluoro-piperidin-1-yl)-methanone,
- (4,4-difluoro-piperidin-1-yl)-[5-(1-isopropyl-piperidin-4-yloxy)-1-(3-trifluoromethoxy-phenyl)-1H-indol-2-yl]-methanone,
- (4,4-difluoro-piperidin-1-yl)-[5-(1-isopropyl-piperidin-4-yloxy)-1-(4-trifluoromethoxy-phenyl)-1H-indol-2-yl]-methanone,
- [1-(2-chloro-pyridin-4-yl)-5-(1-isopropyl-piperidin-4-yloxy)-1H-indol-2-yl]-(4,4-difluoro-piperidin-1-yl)-methanone,
- [1-(6-chloro-pyridin-3-yl)-5-(1-isopropyl-piperidin-4-yloxy)-1H-indol-2-yl]-(4,4-difluoro-piperidin-1-yl)-methanone,
- (4,4-difluoro-piperidin-1-yl)-[5-(1-isopropyl-piperidin-4-yloxy)-1-(2-methoxy-phenyl)-1H-indol-2-yl]-methanone,
- (4,4-difluoro-piperidin-1-yl)-[1-(4-fluoro-phenyl)-5-(1-isopropyl-piperidin-4-yloxy)-1-indol-2-yl]-methanone,
- (4,4-difluoro-piperidin-1-yl)-[1-(3-fluoro-phenyl)-5-(1-isopropyl-piperidin-4-yloxy)-1H-indol-2-yl]-methanone,
- [1-(3-chloro-phenyl)-5-(1-isopropyl-piperidin-4-yloxy)-1H-indol-2-yl]-(4,4-difluoro-piperidin-1-yl)-methanone,
- (4,4-difluoro-piperidin-1-yl)-[5-(1-isopropyl-piperidin-4-yloxy)-1-(3-methoxy-phenyl)-1H-indol-2-yl]-methanone,
- (4,4-difluoro-piperidin-1-yl)-[5-(1-isopropyl-piperidin-4-yloxy)-1-(4-trifluoromethyl-phenyl)-1H-indol-2-yl]-methanone,
- (4,4-difluoro-piperidin-1-yl)-[5-(1-isopropyl-piperidin-4-yloxy)-1-phenyl-1H-indol-2-yl]-methanone,
- (4,4-difluoro-piperidin-1-yl)-[5-(1-isopropyl-piperidin-4-yloxy)-1-p-tolyl-1H-indol-2-yl]-methanone,
- [1-(4-chloro-phenyl)-5-(1-isopropyl-piperidin-4-yloxy)-1H-indol-2-yl]-(4,4-difluoro-piperidin-1-yl)-methanone
- [1-(3,4-dichloro-phenyl)-5-(1-isopropyl-piperidin-4-yloxy)-1H-indol-2-yl]-(4,4-difluoro-piperidin-1-yl)-methanone,
- 5-[2-(4,4-difluoro-piperidine-1-carbonyl)-5-(1-isopropyl-piperidin-4-yloxy)-indol-1-yl]-pyridine-2-carbonitrile,
- (4,4-difluoro-piperidin-1-yl)-[5-(1-isopropyl-piperidin-4-yloxy)-1-(4-methoxy-phenyl)-1H-indol-2-yl]-methanone,
- 3-[2-(4,4-difluoro-piperidine-1-carbonyl)-5-(1-isopropyl-piperidin-4-yloxy)-indol-1-yl]-benzonitrile,
- 4-[2-(4,4-difluoro-piperidine-1-carbonyl)-5-(1-isopropyl-piperidin-4-yloxy)-indol-1-yl]-benzonitrile,
- [5-(1-isopropyl-piperidin-4-yloxy)-1-phenyl-1H-indol-2-yl]-morpholin-4-yl-methanone,
- [1-(4-chloro-phenyl)-5-(1-isopropyl-piperidin-4-yloxy)-1H-indol-2-yl]-morpholin-4-yl-methanone,
- [1-(3,4-dichloro-phenyl)-5-(1-isopropyl-piperidin-4-yloxy)-1H-indol-2-yl]-morpholin-4-yl-methanone,
- [5-(1-isopropyl-piperidin-4-yloxy)-1-p-tolyl-1H-indol-2-yl]-morpholin-4-yl-methanone,
- [5-(1-isopropyl-piperidin-4-yloxy)-1-(4-methoxy-phenyl)-1H-indol-2-yl]-morpholin-4-yl-methanone,
- 4-[5-(1-isopropyl-piperidin-4-yloxy)-2-(morpholine-4-carbonyl)-indol-1-yl]-benzonitrile,
- 5-[2-(4,4-difluoro-piperidine-1-carbonyl)-5-(1-isopropyl-piperidin-4-yloxy)-indol-1-yl]-2-fluoro-benzonitrile,
- (4,4-difluoro-piperidin-1-yl)-[5-(1-isopropyl-piperidin-4-yloxy)-1-(2-methoxy-pyrimidin-5-yl)-1H-indol-2-yl]-methanone,
- 4,4-difluoro-piperidin-1-yl)-[5-(1-isopropyl-piperidin-4-yloxy)-1-thiophen-3-yl-1H-indol-2-yl]-methanone, (4,4-difluoro-piperidin-1-yl)-[5-(1-isopropyl-piperidin-4-yloxy)-1-pyrimidin-5-yl-1H-indol-2-yl]-methanone,
(4,4-difluoro-piperidin-1-yl)-[5-(1-isopropyl-piperidin-4-yloxy)-1-pyridin-2-yl-1H-indol-2-yl]-methanone,
(4,4-difluoro-piperidin-1-yl)-[5-(1-isopropyl-piperidin-4-yloxy)-1-thiophen-2-yl-1H-indol-2-yl]-methanone,
(4,4-difluoro-piperidin-1-yl)-[5-(1-isopropyl-piperidin-4-yloxy)-1-(6-morpholin-4-yl-pyridin-3-yl)-1H-indol-2-yl]-methanone,
(4,4-difluoro-piperidin-1-yl)-[5-(1-isopropyl-piperidin-4-yloxy)-1-pyridin-3-yl-1H-indol-2-yl]-methanone,
[6-chloro-5-(1-isopropyl-piperidin-4-yloxy)-1-pyrimidin-5-yl-1H-indol-2-yl]-(4,4-difluoro-piperidin-1-yl)-methanone,
[6-chloro-5-(1-isopropyl-piperidin-4-yloxy)-1-pyrimidin-5-yl-1H-indol-2-yl]-(4-hydroxy-4-methyl-piperidin-1-yl)-methanone,
[6-bromo-1-(2-chloro-pyridin-4-yl)-5-(1-isopropyl-piperidin-4-yloxy)-1H-indol-2-yl]-morpholin-4-yl-methanone,
[6-bromo-1-(2-chloro-pyridin-4-yl)-5-(1-isopropyl-piperidin-4-yloxy)-1H-indol-2-yl]-(4,4-difluoro-piperidin-1-yl)-methanone,
[5-(1-cyclobutyl-piperidin-4-yloxy)-1-pyrimidin-5-yl-1H-indol-2-yl]-(4,4-difluoro-piperidin-1-yl)-methanone,
(4-hydroxy-4-methyl-piperidin-1-yl)-[5-(1-isopropyl-piperidin-4-yloxy)-1-pyrimidin-5-yl-1H-indol-2-yl]-methanone, and
[5-(1-cyclobutyl-piperidin-4-yloxy)-1-pyrimidin-5-yl-1H-indol-2-yl]-(4-hydroxy-4-methyl-piperidin-1-yl)-methanone,
and pharmaceutically acceptable salts thereof.

19. A process for the manufacture of compounds according to formula Ia or formula Ib, comprising the steps of:
a) treating a compound of the formula II

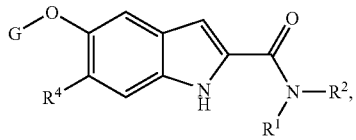

II wherein $R^1$, $R^2$ and $R^4$ are as defined in claim 1, with a suitable base in a suitable solvent under anhydrous conditions and reacting the intermediate anion with an alkylating or acylating agent of the formula III $R^3$—X    III, wherein X signifies a leaving group and $R^3$ is selected from the group consisting of lower hydroxyalkyl, lower cyanoalkyl, optionally substituted lower phenylalkyl, lower alkoxycarbonyl and optionally substituted phenylsulfonyl,

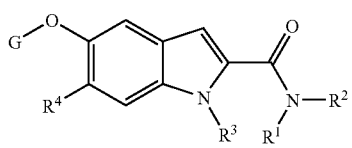

Ia wherein $R^3$ is selected from the group consisting of lower hydroxyalkyl, lower cyanoalkyl, optionally substituted lower phenylalkyl, lower alkoxycarbonyl and optionally substituted phenylsulfonyl,
and if desired,
converting the compound obtained into a pharmaceutically acceptable acid addition salt, or alternatively,
b) reacting a compound of formula II

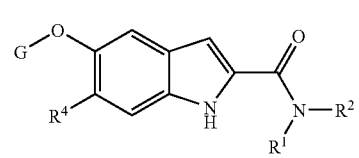

II wherein $R^1$, $R^2$ and $R^4$ are as defined in claim 1, with an optionally substituted phenyl- or heteroaryl boronic acid of the formula IV

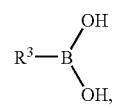

IV wherein $R^3$ signifies optionally substituted aryl or heteroaryl, in the presence of a catalyst and basic conditions to obtain a compound of the formula

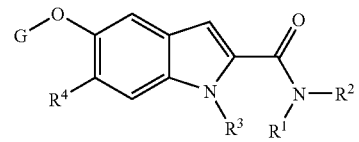

Ib wherein $R^3$ signifies optionally substituted aryl or optionally substituted heteroaryl, and if desired,
converting the compound obtained into a pharmaceutically acceptable acid addition salt.

20. A pharmaceutical composition, comprising a therapeutically effective amount of a compound according to claim 1 and a pharmaceutically acceptable carrier and/or adjuvant.

21. A method for the treatment of obesity in a human being or animal, comprising the step of administering a therapeutically effective amount of a compound according to claim 1 in combination or association with a therapeutically effective amount of a compound selected from the group consisting of a lipase inhibitor, an anorectic agent, a selective serotonin reuptake inhibitor and an agent that stimulates metabolism of body fat, to said human being or animal in need thereof.

22. A method of treatment of type II diabetes in a human being or animal, comprising the step of administering a therapeutically effective amount of a compound according to claim 1 in combination or association with a therapeutically effective amount of an anti-diabetic agent to said human being or animal in need thereof.

* * * * *